United States Patent
Badylak et al.

(10) Patent No.: US 9,277,999 B2
(45) Date of Patent: Mar. 8, 2016

(54) JOINT BIOSCAFFOLDS

(75) Inventors: Stephen F. Badylak, Pittsburgh, PA (US); Bryan N. Brown, Pittsburgh, PA (US); William L. Chung, Mars, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 12/714,195

(22) Filed: Feb. 26, 2010

(65) Prior Publication Data
US 2010/0222882 A1 Sep. 2, 2010

Related U.S. Application Data

(60) Provisional application No. 61/156,162, filed on Feb. 27, 2009.

(51) Int. Cl.
*A61F 2/08* (2006.01)
*A61F 2/30* (2006.01)
(Continued)

(52) U.S. Cl.
CPC ............ *A61F 2/3099* (2013.01); *A61L 27/3633* (2013.01); *A61L 27/48* (2013.01); *A61L 27/58* (2013.01); *A61F 2/30942* (2013.01); *A61F 2002/30062* (2013.01); *A61F 2002/30069* (2013.01); *A61F 2002/3092* (2013.01); *A61F 2002/30113* (2013.01); *A61F 2002/30125* (2013.01); *A61F 2002/30574* (2013.01); *A61F 2002/30576* (2013.01); *A61F 2002/30581* (2013.01); *A61F 2002/30588* (2013.01); *A61F 2002/30754* (2013.01);
(Continued)

(58) Field of Classification Search
CPC ....... A61F 2/0062; A61F 2/28; A61F 2/3872; A61F 2/3099; A61F 2/3094; A61F 2/3877; A61F 2/389; A61F 2/30756; A61F 2002/30754; A61F 2002/30761; A61F 2002/30764; A61F 2002/30766; A61F 2002/30751
USPC .................................. 623/14.12, 23.72–23.76
See application file for complete search history.

(56) References Cited

U.S. PATENT DOCUMENTS 4,502,161 A 3/1985 Wall
4,651,736 A 3/1987 Sanders
(Continued)

FOREIGN PATENT DOCUMENTS

AU 2002316696 B2 3/2003
AU 2002320512 B2 3/2003
(Continued)

OTHER PUBLICATIONS

Brown et al. The Basement Membrane Component of Biologic Scaffolds Derived from Extracellular Matrix. Tissue Engineering. 2006, 519-526, vol. 12, No. 3.
(Continued)

*Primary Examiner* — Alvin Stewart
(74) *Attorney, Agent, or Firm* — Klarquist Sparkman, LLP

(57) ABSTRACT

Provided herein are compositions and medical devices, and in particular, biodegradable scaffolds capable of repairing and replacing cartilagenous meniscuses. Also provided herein are methods of using scaffolds for treating degenerative tissue disorders. In certain embodiments, such scaffolds can promote tissue regeneration of a temporal mandibular joint (TMJ) meniscus.

33 Claims, 18 Drawing Sheets

(51) Int. Cl.
*A61L 27/36* (2006.01)
*A61L 27/48* (2006.01)
*A61L 27/58* (2006.01)

(52) U.S. Cl.
CPC *A61F 2210/0004* (2013.01); *A61F 2230/0006* (2013.01); *A61F 2230/0008* (2013.01); *A61L 2430/06* (2013.01)

(56) References Cited

U.S. PATENT DOCUMENTS

| | | | |
|---|---|---|---|
| 4,778,472 A | 10/1988 | Homsy et al. | |
| 4,902,508 A | 2/1990 | Badylak et al. | |
| 4,919,667 A * | 4/1990 | Richmond | 623/14.12 |
| 4,919,668 A | 4/1990 | Rosenbaum et al. | |
| 4,956,178 A | 9/1990 | Badylak et al. | |
| 5,281,422 A | 1/1994 | Badylak et al. | |
| 5,290,271 A * | 3/1994 | Jernberg | 604/891.1 |
| 5,352,463 A * | 10/1994 | Badylak et al. | 424/551 |
| 5,372,821 A | 12/1994 | Badylak et al. | |
| 5,543,158 A * | 8/1996 | Gref et al. | 424/501 |
| 5,554,389 A | 9/1996 | Badylak et al. | |
| 5,573,784 A | 11/1996 | Badylak et al. | |
| 5,593,445 A | 1/1997 | Waits | |
| 5,645,860 A | 7/1997 | Knapp, Jr. et al. | |
| 5,753,267 A | 5/1998 | Badylak et al. | |
| 5,762,966 A | 6/1998 | Knapp, Jr. et al. | |
| 5,771,969 A | 6/1998 | Garay | |
| 5,800,537 A * | 9/1998 | Bell | 424/93.1 |
| 5,866,414 A | 2/1999 | Badylak et al. | |
| 5,888,220 A | 3/1999 | Felt et al. | |
| 6,099,567 A | 8/2000 | Badylak et al. | |
| 6,165,225 A * | 12/2000 | Antanavich et al. | 623/23.72 |
| 6,176,880 B1 | 1/2001 | Plouhar et al. | |
| 6,248,131 B1 | 6/2001 | Felt et al. | |
| 6,265,333 B1 * | 7/2001 | Dzenis et al. | 442/346 |
| 6,267,786 B1 | 7/2001 | Stone | |
| 6,482,231 B1 | 11/2002 | Abatangelo et al. | |
| 6,485,723 B1 | 11/2002 | Badylak et al. | |
| 6,576,265 B1 | 6/2003 | Spievack | |
| 6,579,538 B1 | 6/2003 | Spievack | |
| 6,638,312 B2 * | 10/2003 | Plouhar et al. | 623/23.72 |
| 6,696,270 B2 | 2/2004 | Badylak et al. | |
| 6,783,776 B2 | 8/2004 | Spievack | |
| 6,793,939 B2 | 9/2004 | Badylak | |
| 6,849,273 B2 | 2/2005 | Spievack | |
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 6,902,932 B2 | 6/2005 | Altman et al. | |
| 6,984,393 B2 | 1/2006 | Amsden | |
| 7,163,563 B2 | 1/2007 | Schwartz et al. | |
| 7,217,294 B2 | 5/2007 | Kusanagi et al. | |
| 7,361,195 B2 | 4/2008 | Schwartz et al. | |
| 7,371,400 B2 | 5/2008 | Borenstein et al. | |
| 7,476,250 B1 | 1/2009 | Mansmann | |
| 7,579,189 B2 | 8/2009 | Freyman et al. | |
| 7,737,060 B2 | 6/2010 | Strickler et al. | |
| 7,803,182 B2 * | 9/2010 | Dave et al. | 623/1.38 |
| 7,819,918 B2 * | 10/2010 | Malaviya et al. | 623/14.12 |
| 7,838,630 B2 | 11/2010 | Murray et al. | |
| 7,931,683 B2 * | 4/2011 | Weber et al. | 623/1.42 |
| 7,955,382 B2 * | 6/2011 | Flanagan et al. | 623/1.42 |
| 7,959,941 B2 | 6/2011 | Knaack et al. | |
| RE42,575 E | 7/2011 | Vacanti et al. | |
| 8,012,205 B2 | 9/2011 | Plouhar et al. | |
| 8,012,211 B2 * | 9/2011 | Kuslich | 623/17.12 |
| 8,025,896 B2 * | 9/2011 | Malaviya et al. | 424/423 |
| 8,105,086 B2 | 1/2012 | Asgary | |
| 8,166,627 B2 | 5/2012 | Deffrennes | |
| 8,366,787 B2 * | 2/2013 | Brown et al. | 623/23.72 |
| 2001/0004710 A1 | 6/2001 | Felt et al. | |
| 2003/0023316 A1 * | 1/2003 | Brown et al. | 623/23.72 |
| 2003/0033021 A1 * | 2/2003 | Plouhar et al. | 623/23.57 |
| 2003/0036797 A1 | 2/2003 | Malaviya et al. | |
| 2004/0143344 A1 * | 7/2004 | Malaviya et al. | 623/23.72 |
| 2004/0267277 A1 | 12/2004 | Zannis et al. | |
| 2005/0043808 A1 | 2/2005 | Felt et al. | |
| 2005/0123588 A1 * | 6/2005 | Zhu et al. | 424/443 |
| 2005/0182463 A1 * | 8/2005 | Hunter et al. | 607/115 |
| 2005/0222688 A1 * | 10/2005 | Zilla et al. | 623/23.72 |
| 2005/0267565 A1 * | 12/2005 | Dave et al. | 623/1.15 |
| 2005/0281781 A1 * | 12/2005 | Ostroff | 424/93.2 |
| 2006/0015187 A1 * | 1/2006 | Hunter et al. | 623/23.5 |
| 2007/0026053 A1 | 2/2007 | Pedrozo et al. | |
| 2007/0042341 A1 * | 2/2007 | Xu et al. | 435/2 |
| 2007/0134209 A1 * | 6/2007 | Oakey | 424/93.7 |
| 2007/0254009 A1 * | 11/2007 | Rubsamen | 424/423 |
| 2007/0282455 A1 * | 12/2007 | Luginbuehl et al. | 623/23.72 |
| 2007/0299517 A1 | 12/2007 | Davisson et al. | |
| 2008/0031923 A1 | 2/2008 | Murray et al. | |
| 2008/0039954 A1 | 2/2008 | Long et al. | |
| 2008/0058955 A1 * | 3/2008 | Shirley et al. | 623/23.72 |
| 2008/0107744 A1 * | 5/2008 | Chu | 424/489 |
| 2008/0140094 A1 | 6/2008 | Schwartz et al. | |
| 2008/0172131 A1 * | 7/2008 | Trieu et al. | 623/23.73 |
| 2008/0213377 A1 * | 9/2008 | Bhatia et al. | 424/489 |
| 2008/0260831 A1 | 10/2008 | Badylak et al. | |
| 2008/0305545 A1 | 12/2008 | Lendlein et al. | |
| 2009/0011486 A1 | 1/2009 | Bettinger et al. | |
| 2009/0035855 A1 * | 2/2009 | Ying et al. | 435/377 |
| 2009/0041851 A1 * | 2/2009 | Costantino et al. | 424/501 |
| 2009/0043398 A1 | 2/2009 | Yakimicki et al. | |
| 2009/0053279 A1 * | 2/2009 | Badylak et al. | 424/423 |
| 2009/0138074 A1 | 5/2009 | Freyman et al. | |
| 2009/0196901 A1 | 8/2009 | Guilak et al. | |
| 2009/0240337 A1 | 9/2009 | Myung et al. | |
| 2009/0252777 A1 | 10/2009 | Taft et al. | |
| 2009/0263468 A1 * | 10/2009 | McAnulty et al. | 424/443 |
| 2010/0023126 A1 | 1/2010 | Grotz | |
| 2010/0036492 A1 | 2/2010 | Hung et al. | |
| 2010/0055144 A1 * | 3/2010 | Sakamoto et al. | 424/423 |
| 2010/0057219 A1 * | 3/2010 | Lee | 623/23.76 |
| 2010/0086578 A1 | 4/2010 | Nielsen et al. | |
| 2010/0151573 A1 * | 6/2010 | King et al. | 435/375 |
| 2010/0179667 A1 * | 7/2010 | Day et al. | 623/23.72 |
| 2010/0204432 A1 | 8/2010 | Younes et al. | |
| 2010/0215713 A1 * | 8/2010 | Dolmans-Van Der Vorst et al. | 424/423 |
| 2010/0222882 A1 * | 9/2010 | Badylak et al. | 623/14.12 |
| 2010/0266654 A1 * | 10/2010 | Hodde et al. | 424/405 |
| 2011/0014267 A1 | 1/2011 | Everland et al. | |
| 2011/0027172 A1 * | 2/2011 | Wang et al. | 424/1.29 |
| 2011/0038939 A1 * | 2/2011 | Lvov et al. | 424/490 |
| 2011/0054408 A1 | 3/2011 | Wei et al. | |
| 2011/0093073 A1 | 4/2011 | Gatt et al. | |
| 2011/0166673 A1 * | 7/2011 | Patel et al. | 623/23.72 |
| 2011/0224801 A1 | 9/2011 | Mansmann | |
| 2011/0245929 A1 | 10/2011 | Rakin et al. | |
| 2012/0003324 A1 | 1/2012 | Campbell et al. | |
| 2012/0185050 A1 | 7/2012 | Schwartz | |
| 2012/0316645 A1 | 12/2012 | Grotz | |
| 2014/0222149 A1 | 8/2014 | Amis et al. | |
| 2014/0309739 A1 | 10/2014 | Badylak et al. | |

FOREIGN PATENT DOCUMENTS

| | | |
|---|---|---|
| AU | 2003204827 B2 | 7/2003 |
| AU | 2007212085 B2 | 8/2007 |
| AU | 2008255147 A1 | 1/2009 |
| EP | 0815203 A1 | 1/1998 |
| EP | 1196206 | 1/2001 |
| EP | 1276486 | 11/2001 |
| EP | 1270025 A2 | 1/2003 |
| EP | 1976459 | 7/2007 |
| EP | 2029728 | 11/2007 |
| EP | 2422823 A1 | 2/2012 |
| GB | 2480682 A | 11/2011 |
| JP | 2011515162 A | 5/2011 |
| JP | 2011519931 A | 7/2011 |

(56) References Cited

FOREIGN PATENT DOCUMENTS

| | | | |
|---|---|---|---|
| JP | 2011224398 A | 11/2011 | |
| WO | 0100783 A2 | 1/2001 | |
| WO | 2006026325 A2 | 3/2006 | |
| WO | 2006093151 A1 | 9/2006 | |
| WO | 2006109137 A1 | 10/2006 | |
| WO | 2008008266 A2 | 1/2008 | |
| WO | 2008024640 A2 | 2/2008 | |
| WO | 2008086147 A1 | 7/2008 | |
| WO | 2010078041 A1 | 7/2010 | |
| WO | 2010104576 A1 | 9/2010 | |
| WO | 2011003422 A1 | 1/2011 | |
| WO | 2011011482 A2 | 1/2011 | |
| WO | 2011041240 A1 | 4/2011 | |
| WO | 2011109712 A2 | 9/2011 | |

OTHER PUBLICATIONS

Brown et al. Surface Characterization of Extracellular Matrix Scaffolds. Biomaterials. 2010, 428-437, vol. 31.
Doede et al. Unsuccessful Alloplastic Esophageal Replacement With Porcine Small Intestine Submucosa. Artificial Organs. 2009, 328-333, vol. 33, No. 4.
Schallberger et al. Effect of Porcine Small Intestine Submucosa on Acute Full=Thickness Wounds in Dogs. 2008. Veterinary Surgery, 515-524, vol. 37.
Soler et al. Early Complications From the Use of Porcine Dermal Collagen Implants (Permacol) as Bridging Constructs in the Repair of Massive Rotator Cuff Tears. A Report of 4 Cases. Acta. Orthop. Belg. 2007, 432-436, vol. 73.
Walton et al. Restore Orthobiologic Implant: Not Recommended for Augmentation of Rotator Cuff Repairs. Journal of Bone and Joint Surgery. 2007, 786-791, vol. 89.
Almarza et al. Design Characteristics for the Tissue Engineering of Cartilaginous Tissues, Annals of Biomedical Engineering, Jan. 2004, pp. 2-17, vol. 32, No. 1.
Dolwick et al. Silicone-induced foreign body reaction and lymphadenopathy after temporomandibular joint arthroplasty, Oral Surg. Oral Med. Oral Pathol., May 1985, pp. 449-452, vol. 59.
Gilbert et al. Production and characterization of ECM powder: implications for tissue engineering applications, Biomaterials, 2005, pp. 1431-1436, vol. 26.
Heffez et al. CT Evaluation of TMJ Disc Replacement with a Proplast-Teflon Laminate, J. Oral Maxillofac. Surg., 1987, pp. 657-665, vol. 45.
Ryan, Alloplastic Implants in the Temporomandibular Joint, Disorders of the TMJ II: Arthrotomy, Dec. 1989, pp. 427-441, vol. 1, No. 2.
Wagner et al. Assessment of Proplast-Teflon Disc Replacements, J. Oral Maxillofac. Surg., 1990, pp. 1140-1144, vol. 48.
Westesson et al. Destructive lesions of the mandibular condyle following diskectomy with temporary silicone implant, Oral. Surg. Oral Med. Oral Pathol., Feb. 1987, pp. 143-150, vol. 63, No. 2.
Wood et al. Use of a particulate extracellular matrix bioscaffold for treatment of acquired urinary incontinence in dogs, JAVMA, Apr. 1, 2005, pp. 1095-1097, vol. 226, No. 7.
Partial replacement of the meniscus of the knee using a biodegradable scaffold. National Institute for Health and Clinical Excellentce. Jul. 2012.
National Medical Policy. Collagen Meniscal Implant (e.g. Meneflex). Jul. 2009. Center for Medicare and Medicaid Services.
Almarza et al. Design characteristics for the tissue engineering of cartilaginous tissue. Ann. Biomed. Eng. 2004; vol. 32, No. 1, 2-17.
Brophy et al. Surgical options for meniscal replacement. J Am. Acad. Orth. Surg. 2012; vol. 20, No. 5, 265-272.
Harston et al. Collagen meniscus implantation: a systematic review including rehabilitation and return to sports activity. Knee Surg. Sports Traumatol. Arthrosc. 2012; vol. 20, 135-146.
Johns et al. Design characteristics for temporomandibular joint disc tissue engineering: learning from tendon and articular cartilage. Proc. IMechE 2007; vol. 221, part H, 509-526.
Lai et al. Histological analysis of regeneration of temporomandibular joint discs in rabbits by using a reconstituted collagen template. Int. J. Oral Maxillofac. Surg. 2005; vol. 34, 311-320.
Lumpkins et al. A mechanical evaluation of three decellularization methods in the design of a xenographic scaffold for tissue engineering the temporomandibular joint disc. Acta Biomaterialia 2008; vol. 4, 808-816.
Monllau et al. Outcome after partial medial meniscus substitution with the collagen meniscal implant at a minimum of 10 years' follow-up. J Arthrosc. Related Surg. 2011; vol. 27, No. 7, 933-943.
Rodkey et al. Comparison of the collagen meniscus implant with partial meniscectomy. J. Bone Joint Surg. 2008; vol. 90, 1413-1426.
Stone et al. Meniscal regeneration with copolymeric collagen scaffolds. Am. J. Sports Med. 1992; vol. 20, No. 2, 104-111.
Zaffagnini et al. New approaches to meniscal surgery: meniscal substitution and transplantation. Sports Med. J. 2012; 110-113.

* cited by examiner

| Specimen | Native Canine TMJ Disc | | | | | | Remodeled UBM Scaffold | | | Pre-implantation UBM scaffold | | | | | |
|---|---|---|---|---|---|---|---|---|---|---|---|---|---|---|---|
| | 1 | 2 | 3 | 4 | 5 | 6 | 1 | 2 | 3 | 1 | 2 | 3 | | 5 | 6 |
| Modulus (kPa) | 25 | 20 | 14 | 26 | 32 | 24 | 33 | 58 | 32 | 193 | 197 | 128 | | 246 | 137 |
| % Stress Relaxation | 48 | 32 | 54 | 35 | 50 | 54 | 34 | 58 | 26 | 30 | 30 | 33 | | 30 | 35 |
| % Collagen per dry weight | 83 | 64 | 81 | 51 | 42 | 50 | 41 | 40 | 66 | 68 | 78 | 53 | | 95 | 32 |
| % GAG per weight | 0.7 | 0.4 | 0.7 | 0.4 | 0.5 | 0.6 | 0.9 | 1.0 | 1.1 | 0.4 | 0.7 | 0.2 | | 0.7 | 0.3 |
| % H₂0 by weight | 82 | 75 | 80 | 83 | 78 | 68 | 81 | 81 | 86 | 78 | 82 | 49 | | 85 | 54 |

Fig.22A

|  | Native Canine TMJ disc | Remodeled UBM scaffold | Pre-implantation UBM scaffold |
| --- | --- | --- | --- |
| Modulus (kPa) | 23.4 ± 6.0 | 41.2 ± 14.8 | 180.0 ± 48.3 |
| % Stress Relaxation | 45.4 ± 9.5 | 39.6 ± 16.5 | 31.4 ± 2.2 |
| % Collagen per dry weight | 62.0 ± 17.4 | 49.0 ± 14.3 | 59.7 ± 30.0 |
| % GAG per weight | 0.55 ± 0.11 | 1.01 ± 0.09 | 0.47 ± 0.23 |
| % $H_2O$ by weight | 77.6 ± 5.3 | 82.6 ± 2.8 | 69.5 ± 16.7 |

Fig. 22B

JOINT BIOSCAFFOLDS

This application claims the benefit under 35 U.S.C. §119 (e) to U.S. Provisional Patent Application No. 61/156,162, filed Feb. 27, 2009, which is incorporated herein by reference in its entirety.

This invention was made with government support under Grant #SAP 4100045998 awarded by the Commonwealth of Pennsylvania. The government has certain rights in the invention.

The temporomandibular joints (TMJs) connect the jaw to the skull and generate large amounts of force in the jaw. In between these two bones rests a fibrocartilagenous disc termed the TMJ meniscus, which acts to disperse the forces on the jaw and reduce friction during movement. In anatomy, a meniscus is a fibrocartilagenous structure present, e.g., in the knee, acromioclavicular, and sternoclavicular joints that, in contrast to articular discs, only partly divides a joint cavity.

The TMJs are unusual because they are one of the only synovial joints in the human body comprising a disc meniscus. The disc separates the lower joint compartment formed by the mandible and the articular disc (allowing rotational movement) from the upper joint compartment (allowing translational movements). The top of the mandible which mates to the under-surface of the disc is termed the "condyle" and the temporal bone of the skull that mates to the upper surface of the disk is termed the "glenoid (or mandibular) fossa." The TMJ meniscus differs substantially from other meniscuses such as the knee meniscus, as it comprises almost entirely type I collagen as opposed to approximately 80% type 1120% type II collagen in the knee.

Temporomandibular joint disorder or dysfunction (TMD) occurs when there is pain at or near the temporomandibular joint. Broadly, TMD comprises a group of disorders involving the joints, muscles, tendons, ligaments, and blood vessels at the joint. One type of disorder of the TMJ is internal derangement (ID), which involves an abnormality of the meniscus-temporal fossa relationship, resulting in a mechanical disorder that creates irregular joint noises and prohibits normal condylar movement. Although the etiology remains obscure, various inflammatory mediators have been implicated. For example, synovial fluid analysis indicates a role of cytokines and proteinases in development of ID. Moreover, interleukins have been detected in both ID and rheumatoid arthritis of the TMJ. One possible mechanism is the inducing release of proteinases and collagenases by inflammatory cytokines. Despite this understanding, treatment for such derangement is usually surgical.

For example, internal derangement due to ankylosis, meniscal perforation, and degenerative joint disease, among others, can be treated by a meniscectomy Complications arising from meniscectomy without replacement include heterotopic bone formation and joint ankylosis. The rationale for replacing the TMJ meniscus with a substitute material is to protect the articular surfaces from further degenerative changes and to avoid joint adhesion formation. Many alloplastic materials such as SILASTIC™, silicone and PROPLAST™-Teflon, have been used to replace the TMJ meniscus but results have been less than satisfactory. Often times, joint pathology is more severe following the placement of such devices. Autograft tissues have been used both as disc replacement materials following meniscectomy and as interpositional materials in the treatment of joint ankylosis. Sources such as the temporalis muscle flap, auricular cartilage, and dermis have proven far better options than their alloplastic counterparts but still have the obvious disadvantage of morbidity associated with the graft donor site. Furthermore, a variety of studies have shown fibrosis or, in the case of the temporalis muscle flap, necrosis and devitalization of autogenous tissue grafts.

Thus, what is needed is a graft material for the treatment of TMJ pathology with associated meniscus abnormality is a scaffold for cellular influx and that would be readily implanted without the associated morbidity of autogenous tissue harvest. It is also desirable that the graft closely match the natural state of the disc which is hypovascular, aneural, and alymphatic while being able to function mechanically immediately after implantation.

SUMMARY

Extracellular matrix (ECM) scaffolds for cartilagenous tissue regeneration and replacement are disclosed herein. In certain embodiments the scaffolds comprise a particulate and/or gel ECM core encapsulated within an ECM sheath. The core can be a particulate/powdered material, a gel material or both, and in each case, the core and/or the sheath optionally comprise cells, such as one or more of stem cells, progenitor cells and differentiated cells, such as fibroblasts and chondrocytes. The encapsulation of particulate ECM allows for the structure to operate in three-dimensions as well as deform elastically in response to compressive and shear forces, and, thus, respond to biomechanical stresses much like the original bodily tissues. The compositions are compatible with any desired shape consistent with any suitable method.

In certain embodiments, the scaffold can be tailored to the particular anatomy of an individual and thus can be designed to operate as an implant device. As such, it can operate as an implant device which replaces fibrocartilagenous meniscuses in the temporomandibular joints (TMJs) and also provides a substrate onto which cartilage producing cells can attach and repair and/or replace the original joint meniscus. One particularly useful replacement is of a temporomandibular joint meniscus following meniscectomy.

In yet other embodiments, ECM scaffolds comprise particulate and/or gel ECM encapsulated within a sheath comprising xenogenic or allogeneic ECM sheets. The particulate ECM and ECM sheaths comprise both the structural and functional proteins present within native mammalian ECM. The ECM may be derived from mammalian tissue sources such as, without limitation, the urinary bladder, esophagus, skin, liver, spleen, heart, pancreas, ovary, and blood vessels. Sources of the ECM may include, without limitation, any warm blooded vertebrate, such as pig, cow, horse, or monkey. In one embodiment, both the particulate ECM and the encapsulating ECM sheath are derived from porcine urinary bladder matrix (UBM).

As disclosed herein, ECM compositions facilitate influx of cells into the implanted devices, thereby constructively remodeling the ECM device into fibrocartilagenous tissue that conforms to the desired shape. Likewise a method of promoting wound healing or tissue generation or regeneration in a patient is provided comprising contacting an implant as described herein with cells in vitro (for instance, ex vivo for autologous cells), culturing the cells in vitro so that the cells grow in and/or on the scaffold. Useful cell types include fibroblasts, chondrocytes and stem or progenitor cells.

In addition, surgical methods of replacing a joint meniscus and treating temporomandibular joint disease are provided. In a one embodiment, a temporo-mandibular joint meniscus is removed and replaced with a three-dimensional tissue scaffold comprised of a particulate and/or gel ECM core encapsulated within an ECM sheath. Thus, the scaffold acts as a structurally and functionally normal meniscus while facilitating influx of cells into the scaffold. In the one embodiment, the temporomandibular joint meniscus is replaced or repaired.

According to certain embodiments, the scaffolds are biodegradable, elastomeric, porous and biocompatible. Also provided are methods of preparing biodegradable elastomeric scaffolds and promoting wound healing and/or tissue regeneration within a patient. The method comprises implanting a biodegradable elastomeric scaffold at, around or near a site in need of wound healing, tissue remodeling and/or tissue regeneration. In another non-limiting embodiment, such a scaffold comprises cells. For example and without limitation, such a method comprises culturing cells in and/or on a biodegradable elastomeric scaffold in vitro and implanting the scaffold. In yet another non-limiting embodiment, the biodegradable elastomeric scaffold comprises bioactive or therapeutic agents, such as, without limitation growth factors, antibiotics, and anti-inflammatory agents.

According to certain non-limiting embodiments, the biological polymeric component is an extracellular matrix material. The ECM-derived material may be isolated from, for example and without limitation, urinary bladder tissue. In one non-limiting embodiment, the extracellular matrix material comprises decellularized epithelial basement membrane and subjacent tunica propria. In another embodiment, the extracellular matrix-derived material comprises tunica submucosa. In yet another embodiment, extracellular matrix-derived material comprises epithelial basement membrane, subjacent tunica propria and tunica submucosa. In certain non-limiting embodiments, the extracellular matrix-derived material is isolated from small intestinal submucosa or the dermis of skin.

In certain embodiments, the device resembles a hat in which there is a core center section and a brim which extends from the core. In such structures, three ultrastructural parameters operate in unison to allow an articulating device to function even from the moment of implantation: the height and composition of the core which modulates compressive force, the diameter of circular core, including the major and minor diameters where the core is elliptical, which modulates the lateral displacement at the site of implantation, and the radius of the brim which modulates the type and number of attachment points for the device in the implant site. Moreover, the functionality of the device is not degraded over time, as the microstructure allows for influx of cells, thus allowing the body to remodel the device to the unique anatomy of each implanted individual.

BRIEF DESCRIPTION OF THE DRAWINGS

FIG. 9 is a schematic for a non-limiting embodiment of a mold for a canine TMJ meniscus replacement device. All measurements are shown in millimeters (mm). The molds creates multiple devices with multiple dimensions at the same time.

FIG. 10 is a schematic for a non-limiting embodiment of a mold for a human TMJ meniscus replacement device. All measurements are shown in millimeters (mm).

FIG. 22A is a tabulation of the data from Example 2. FIG. 22B provides averages and standard deviation.

DETAILED DESCRIPTION

Figure 1A:
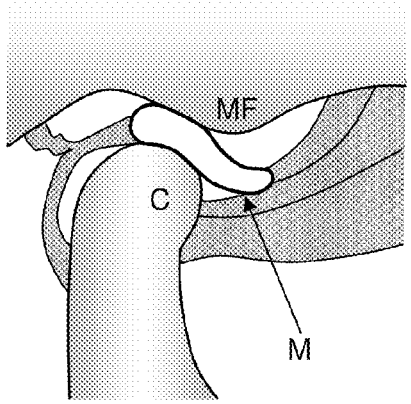
FIG. 1A shows the normal articulation of the TMJ meniscus (M) in relation to the condyle (C) and the mandibular fossa (MF) during jaw movement.
Figure 1A:
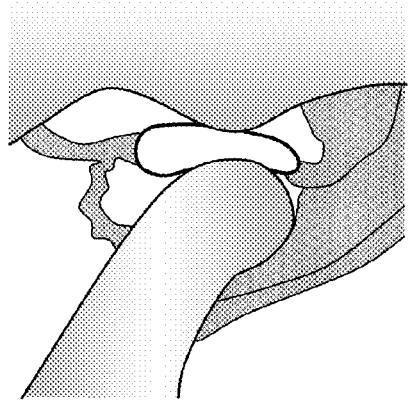
Figure 1B:
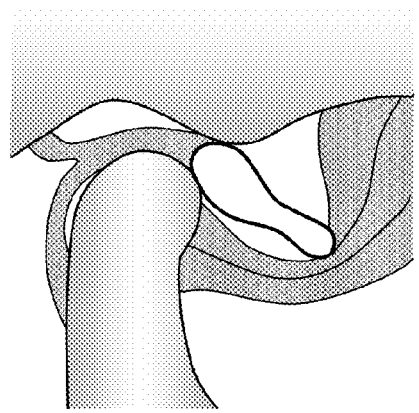
FIG. 1B shows the deranged articulation of the TMJ meniscus where an anterior dislocation of the meniscus with reduction has occurred.
Figure 1B:
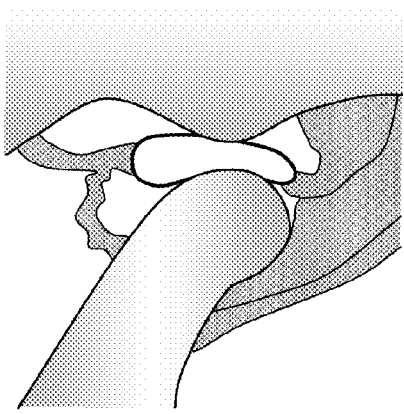
Figure 1C:
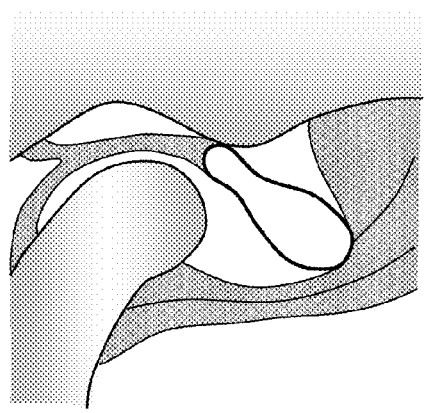
FIG. 1C shows the deranged articulation of the TMJ meniscus where an anterior dislocation of the meniscus without reduction has occurred.
Figure 1C:
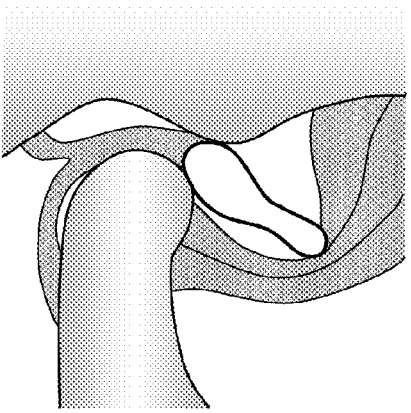

Described herein are scaffolds suitable for use in tissue engineering and regenerative medicine applications, such as replacement of fibrocartilagenous tissue. Such scaffolds are useful for replacing and repairing cartilagenous discs such as the temporomandibular joint meniscus. Generally, any material that is biocompatible, biodegradable, and has mechanical properties similar to that of native tissue can be used as a scaffold, including for example elastomeric scaffolds. In one embodiment, the scaffold comprises a powdered biological extracellular matrix (ECM) encased in a laminar sheath of ECM. In yet another embodiment, the device consisting of particulate ECM derived from porcine urinary bladder (UBM-ECM) is encased within sheets of UBM-ECM to mimic the shape and size of the native TMJ meniscus. In another non-limiting embodiment, the scaffold comprises bioactive or therapeutic agents.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

Scaffolds can be used for a large number of medical applications including, but not limited to, wound healing, tissue remodeling, and tissue regeneration. For example and without limitation, the scaffold can be used for wound healing. In one non-limiting embodiment, the scaffold comprises bioactive agents to facilitate tissue healing, tissue remodeling and/or angiogenesis. In another non-limiting embodiment, the scaffold comprises bioactive agents to ward off bacteria and other pathogens, recruit selected cell types, such as stem cells, or induce differentiation of cells. In yet another non-limiting embodiment, the scaffold comprises pores to allow a wound to drain or for cells to pass through and deposit connective tissue. In yet another non-limiting embodiment, the scaffold comprises combinations of cells and bioactive agents. In another non-limiting embodiment, combinations of cells and bioactive agents are added to the scaffold before or during implantation at a site in a patient.

As used herein, the term "polymer" refers to both synthetic polymeric components and biological polymeric components. The scaffolds described herein can comprise any suitable combination of synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, a non-woven mesh formed by electrodeposition.

Generally, the polymeric components suitable for the scaffold described herein may be any polymer that is biodegradable and biocompatible. By "biodegradable", it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. Non-limiting examples of biodegradeable polymers include poly(ester urethane) urea elastomers (PEUU) and poly(ether ester urethane) urea elastomers (PEEUU). In other non-limiting embodiments, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain peptides or biomacromolecules as building blocks which are susceptible to chemical reactions once placed in situ. In one non-limiting example, the polymer is a polypeptide comprising the amino acid sequence alanine-alanine-lysine, which confers enzymatic lability to the polymer. In another non-limiting embodiment, the polymer composition may comprise a biomacromolecular component derived from an ECM. For example, the polymer composition may comprise the biomacromolecule collagen so that collagenase, which is present in situ, can degrade the collagen.

The polymer components may be selected so that they degrade in situ on a timescale that is similar to an expected rate of healing of the wound or tissue. Non-limiting examples of in situ degradation rates include between one week and one year or increments therebetween for instance, between two weeks and 10 months, and between one month and six month.

The polymeric components used to make the devices disclosed herein are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products, thereof are not cytotoxic and/or carcinogenic within useful, practical and/or acceptable tolerances. For example, the polymer when placed in a human epithelial cell culture does not adversely affect the viability, growth, adhesion, and number of cells. In one non-limiting embodiment, the compositions, and/or devices are "biocompatible" to the extent they are acceptable for use in a human patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold.

The mechanical properties of a biodegradable scaffold can be optimized to operate under the normal strain and stress on the native tissue at the site of implantation. In certain non-limiting embodiments, the mechanical properties of the scaffold are optimized similar to or identical to that of native soft tissue, such as fascia, connective tissue, blood vessel, muscle, tendon, fat, etc.

The mechanical properties of the scaffold also may be optimized to be suitable for surgical handling. In one non-limiting embodiment, the scaffold is flexible and can be sutured to the site. In another, the scaffold is foldable and can be delivered to the site by minimally invasive laparoscopic methods.

In one non-limiting example, biodegradable scaffolds can be surgically implanted to replace a TMJ meniscus. The implant can be placed by making a preauricular incision while the patient is under general anesthesia. Prior to surgery, the anterior-posterior ("AP") dimension of the condylar head and glenoid fossa can be estimated and then during surgery, the size can be measured for the implant. The implant can be inserted over the condylar head and fixed with slow-resorbing sutures (for example, either 4.0 MERSILINE™ or 4.0 CAPROSYN™, among others) to the zygomatic bone (e.g., the inferolateral surface of the articulating fossa). In certain embodiments, the implant can be secured with three fixation sutures to the zygomatic arch. For example, three holes can be created through the inferolateral surface of the zygomatic bone coincident with the anterior-posterior (AP) dimension of the articulating fossa. Next, a narrow fissure-shaped burr in a rotary instrument under irrigation can be used to create fixation holes for passage of the suture needle through the zygomatic bone. Once the implantation site is prepared, the implant can be placed into the superior joint space and the suture needle can be passed through the lateral extension of the implant. Once in place, the medial brim of the implant can be tucked into the medial aspect of the joint space. For fixation, a suture needle can be placed through the holes in the bone and the brim of the implant, and then the suture can be used to secure the implant to the bone. Finally, the suture can be tied to secure the implant in the fossa. In certain embodiments, one or two additional sutures may be placed laterally through adjacent muscle tissue to add further stability of the implant.

The physical and/or mechanical properties of the biodegradable scaffold can be optimized according to the intended use. Variables that can be optimized include without limitation, the extent of physical, chemical or photooxidative cross-linking in a network comprising polymeric components, the ratio of polymeric components within the network, the distribution of molecular weight of the polymeric components, and the method of processing the polymers. Polymers are typically semicrystalline and their physical properties and/or morphology are dependant upon a large number of factors, including monomer composition, polydispersity, average molecular weight, cross-linking, and melting/crystallization conditions. For example, flow and/or shear conditions during cooling of a polymer melt are known to affect formation of crystalline structures in the composition. In one non-limiting embodiment, the scaffold comprises a polymeric component that provides strength and durability to the scaffold, yet is elastomeric so that the mechanical properties of the scaffold are similar to the native tissue surrounding the wound or site in need of tissue regeneration.

As described herein, according to certain non-limiting embodiments, one or more of the polymeric components of the biodegradable scaffold is elastomeric. In one non-limiting example, the scaffold has physical properties similar to that of cartilage. In certain non-limiting embodiments, the biodegradable scaffold comprises highly distensible polymeric components. Examples of suitable polymers include those that have a breaking strain ranging from about 100% to about 900%, including any increments therebetween, for example between 200% and 800%, or between 325% and 600%. In other non-limiting embodiments, the breaking strain of the polymer is between 50% and 100% including any increments therebetween. Further, it is often useful to select polymers with tensile strengths of from 10 kPa to 30 MPa, including increments therebetween, such as from 5 MPa to 25 MPa, and between 8 MPa and 20 MPa. In certain non-limiting embodiments, the initial modulus is between 10 kPa to 100 MPa and increments therebetween, such as between 10 MPa and 90 MPa, and between 20 MPa and 70 MPa.

The extracellular matrix is useful for promoting cell growth on the scaffold, recruiting appropriate host cells for construction, remodeling, and/or enhancement of biocompatibility. In one non-limiting embodiment, the biological polymeric component comprises and includes an extracellular matrix-derived material. As used herein, the terms "extracellular matrix" and "ECM" refer to a complex mixture of structural and functional biomolecules and/or biomacromolecules including, but not limited to, structural proteins, specialized proteins, proteoglycans, glycosaminoglycans, and growth factors that surround and support cells within mammalian tissues and, unless otherwise indicated, is acellular.

Generally, any type of extracellular matrix (ECM) can be used to prepare the biological, ECM-derived polymeric component of the biodegradable elastomeric scaffold (for example and without limitation, see U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). By "ECM-derived material" it is meant a composition that is prepared from a natural ECM or from an in vitro source wherein the ECM is produced by cultured cells and comprises one or more polymeric components (constituents) of native ECM. ECM preparations can be considered to be "decellularized" or "acellular", meaning the cells have been removed from the source tissue through processes described herein and known in the art.

According to one non-limiting example of the ECM-derived material, ECM is isolated from a vertebrate animal, for example, from a warm blooded mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. The ECM can comprise any portion or tissue obtained from an organ, including, for example and without limitation, submucosa, epithelial basement membrane, tunica propria, etc. In one non-limiting embodiment, the ECM is isolated from urinary bladder, which may or may not include the basement membrane. In another non-limiting embodiment, the ECM includes at least a portion of the basement membrane. In certain non-limiting embodiments, the material that serves as the biological component of the scaffold consists primarily (e.g., greater than 70%, 80%, or 90%) of ECM. In another non-limiting embodiment, the biodegradable elastomeric scaffold may contain at least 50% ECM, at least 60% ECM, at least 70% ECM, and at least 80% ECM. In yet another non-limiting embodiment, the biodegradable elastomeric scaffold comprises at least 10% ECM. The ECM material may or may not retain some of the cellular elements that comprised the original tissue such as capillary endothelial cells or fibrocytes. The type of ECM used in the scaffold can vary depending on the intended cell types to be recruited during wound healing or tissue regeneration, the native tissue architecture of the tissue organ to be replaced, the availability of the tissue source of ECM, or other factors that affect the quality of the final scaffold and the possibility of manufacturing the scaffold. For example and without limitation, the ECM may contain both a basement membrane surface and a non-basement membrane surface, which would be useful for promoting the reconstruction of tissue. In certain embodiments, an implantable device can comprise either a smooth basement membrane surface (luminal) or a rough non-basement membrane surface (abluminal). For example, in applications where the device operates within a synovial joint, a smooth surface for the device can be particularly advantageous.

In one non-limiting embodiment, the ECM is harvested from porcine urinary bladders (also known as urinary bladder matrix or UBM). Briefly, the ECM is prepared by removing the urinary bladder tissue from a pig and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. The relatively fragile epithelial basement membrane is invariably damaged and removed by any mechanical abrasion on the luminal surface. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria.

Figure 2:
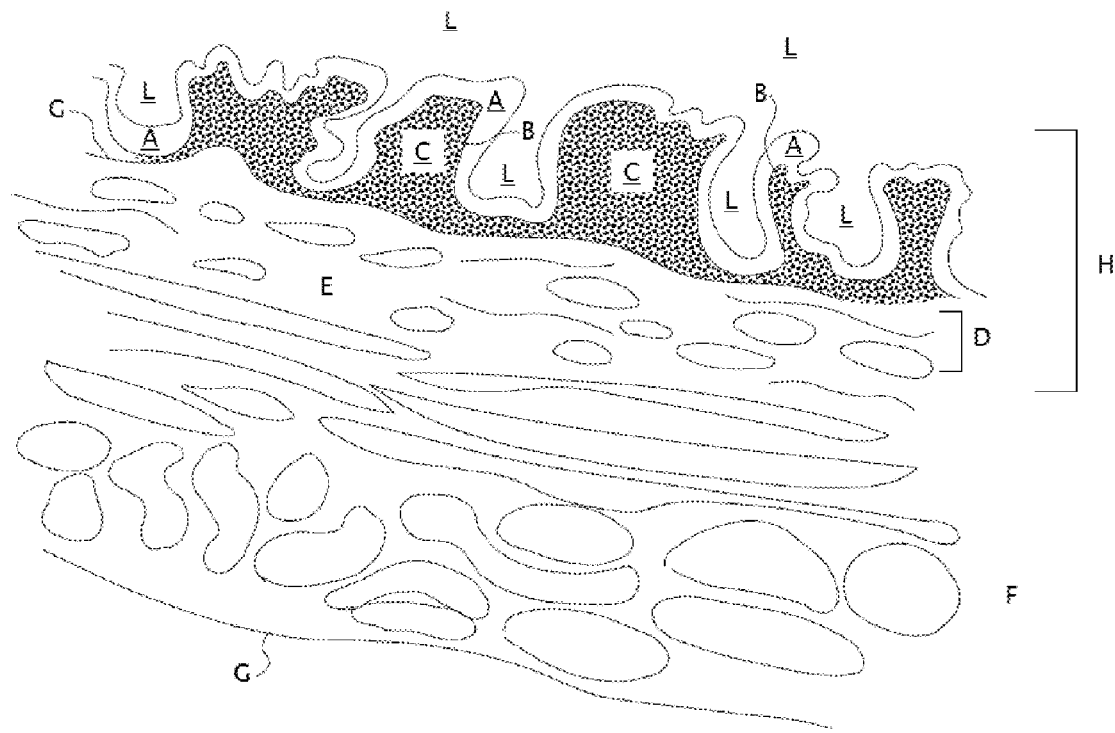
FIG. 2 shows schematically a cross-sectional view of the wall of the urinary bladder (not drawn to scale). The following structures are shown: epithelial cell layer (A), basement membrane (B), tunica propria (C), muscularis mucosa (D), tunica mucosa (E), tunica muscularis externa (F), tunica serosa (G), tunica mucosa (H), and lumen of the bladder (L).

In another embodiment, the ECM is prepared by abrading porcine bladder tissue to remove the outer layers including both the tunica serosa and the tunica muscularis (layers G and F in FIG. 2) using a longitudinal wiping motion with a scalpel handle and moistened gauze. Following eversion of the tissue segment, the luminal portion of the tunica mucosa (layer H in FIG. 2) is delaminated from the underlying tissue using the same wiping motion. Care is taken to prevent perforation of the submucosa (layer E of FIG. 2). After these tissues are removed, the resulting ECM consists mainly of the tunica submucosa (layer E of FIG. 2).

In another embodiment ECM is prepared as a powder. Such powder can be made according to the method of Gilbert et al., Biomaterials 26 (2005) 1431-1435, herein incorporated by reference in its entirety. For example, UBM sheets can be lyophilized and then chopped into small sheets for immersion in liquid nitrogen. The snap frozen material can then be comminuted so that particles are small enough to be placed in a rotary knife mill, where the ECM is powdered. Similarly, by precipitating NaCl within the ECM tissue the material will fracture into uniformly sized particles, which can be snap frozen, lyophilized, and powdered.

According to another embodiment, an extracellular matrix-derived gel is provided. In certain embodiments, the method for making such a gel comprises: (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution, and (iv) gelling the solution at a temperature greater than approximately 25° C. The ECM typically is derived from mammalian tissue, such as, without limitation from one of urinary bladder, spleen, liver, heart, pancreas, ovary, or small intestine. In certain embodiments, the ECM is derived from a pig, cow, horse, monkey, or human. In one non-limiting embodiment, the ECM is lyophilized and comminuted. The ECM is then solubilized with an acid protease. The acid protease may be, without limitation, pepsin or trypsin, and in one embodiment is pepsin. The ECM typically is solubilized at an acid pH suitable or optimal for the protease, such as greater than about pH 2, or between pH 2 and 4, for example in a 0.01M HCl solution. The solution typically is solubilized for 12-48 hours, depending upon the tissue type (e.g., see examples below), with mixing (stirring, agitation, admixing, blending, rotating, tilting, etc.).

Once the ECM is solubilized the pH is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution can be gelled at temperatures approaching 37° C., typically at any temperature over 25° C., though gelation proceeds much more rapidly at temperatures over 30° C., and as the temperature approaches physiological temperature. The method typically does not include a dialysis step prior to gelation, yielding a more-complete ECM-like matrix that typically gels at 37° C. more slowly than comparable collagen or dialyzed ECM preparations.

As described herein, the composition can be molded into any shape by any suitable method, including, without limitation, placing into or onto a mold, electrodeposition, and injection into a cavity or onto a surface in a patient. Further, a molded gel can be trimmed and otherwise shaped by cutting or other suitable methods. In one non-limiting embodiment, the gel is injected into a site on a patient to add additional bulk or to fill in a void, for example, resulting from trauma or from removal or degradation of tissue. In one non-limiting embodiment, the acidic solubilization solution is mixed in a static mixer with a base and/or buffer during injection into a patient. In further embodiments, cells, drugs, cytokines and/or growth factors can be added to the gel prior to, during or after gelation, so long as the bioactivity of the cells, drugs, cytokines and/or growth factors is not substantially or practically (for the intended use) affected by the processing of the gel to its final form.

The ECM can be sterilized by any of a number of standard methods without loss of function. For example and without limitation, the material can be sterilized by propylene oxide or ethylene oxide treatment, gamma irradiation treatment (0.05 to 4 mRad), gas plasma sterilization, peracetic acid sterilization, or electron beam treatment. Treatment with glutaraldehyde results in sterilization as well as increased cross-linking of the ECM. This treatment substantially alters the material such that it is slowly resorbed or not resorbed at all and incites a different type of host remodeling, which more closely resembles scar tissue formation or encapsulation rather than constructive remodeling. If desired, cross-linking of the protein material within the ECM can also be induced with, for example and without limitation, carbodiimide isocyanate treatments, dehydrothermal methods, and photooxidation methods. In one non-limiting embodiment, the ECM is disinfected by immersion in 0.1% (v/v) peracetic acid, 4% (v/v) ethanol, and 96% (v/v) sterile water for two hours. The ECM material is then washed twice for 15 minutes with PBS (pH=7.4) and twice for 15 minutes with deionized water. The ECM-derived material may be further processed by optional drying, desiccation, lyophilization, freeze drying, and/or glassification. The ECM-derived material optionally can be further digested, for example and without limitation by hydration (if dried), acidification, enzymatic digests with, for example and without limitation, trypsin or pepsin and neutralization.

Commercially available ECM preparations can also be used as the biological polymeric component of the scaffold. In one non-limiting embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another non-limiting embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (ACell Corporation; Jessup, Md.).

In general, the biodegradable scaffold described herein may be made using any useful method, including one of the many common processes known in the polymer and textile arts. The biodegradable scaffold may take many different forms. In certain non-limiting embodiments, the biodegradable scaffold comprises a thin, flexible fabric that can be sewn directly on to the site to be treated. In another non-limiting embodiment, the scaffold comprises a non-woven mat that can be sutured in place at the site of implantation or affixed using a medically acceptable adhesive. In one non-limiting embodiment, the scaffold is substantially planar (having much greater dimension in two dimensions and a substantially smaller dimension in a third, comparable to bandages, gauze, and other substantially flexible, flat items). In another non-limiting embodiment, the biodegradable scaffold comprises a non-woven fibrous article formed by electrodeposition of a suspension containing the synthetic polymeric component and the biological polymeric component. In yet another non-limiting embodiment, the biodegradable scaffold comprises a porous composite formed by thermally induced phase separation.

The biodegradable scaffold can also have three-dimensional shapes useful for treating wounds and tissue deficiencies, such as plugs, rings, wires, cylinders, tubes, or disks. A useful range of thickness for the biodegradable scaffold is between from about 10 µm (micrometers or microns (µ)) to about 3.5 cm, including increments therebetween, including, without limitation from about 10 µm to about 50 µm, 50 µm to 3.5 cm, 100 µm to 3.0 cm, and between 300 µm and 2.5 cm.

Figure 3:
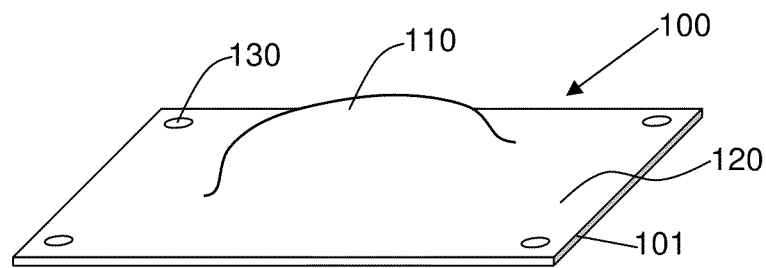
FIG. 3 shows a schematic of one embodiment of a TMJ meniscus replacement device comprising a central core 110 a brim 120 and suture attachment points 130 (holes) in the brim. The device may be attached next to the skull laterally and medially.
Figure 4:
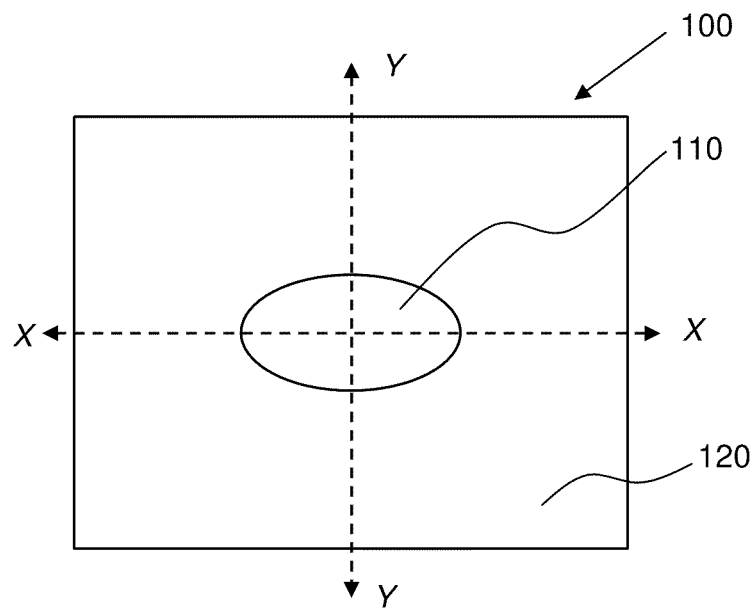
FIG. 4 shows a top-down schematic of one embodiment of a TMJ meniscus replacement device comprising a central core 110 and a brim 120 having a major axis 5 and a minor axis 6.

In certain embodiments, the shape of the device is useful for replacing or repairing cartilagenous disc, such as, for example a temporomandibular joint meniscus. In further embodiments as shown in FIGS. 3 and 4, the disc replacement device 100 comprises an ultrastructure similar to a hat wherein a central core 110 is thick while the surrounding brim 120 is thin. The advantage of the design is that the central core 110 carries the compressive and shear forces between the mandible and the skull, while the brim 120 allows the device anchored at specific points 130 (both laterally as well as medially), and, thus, attached to the surrounding tissue such that it remains in place, but has sufficient movement to allow the mandible to move without grinding against the skull. The brain may also serve as a conduit for the migration and infiltration of cells into the acellular ECM scaffold.

Thus, three ultrastructural parameters operate in unison to allow the device to function even at the moment of implantation: the height and composition of the core which modulates compressive force (e.g., deforms under stress), the diameter of circular core including the major and minor diameters where the core is elliptical which modulates the lateral displacement at the site of implantation, and the radius of the brim which modulates the type and number of attachment points for the device in the implant site. Moreover, the functionality of the device is not degraded over time, as the microstructure allows for influx of cells, thus allowing the body to remodel the device to the unique anatomy of each implanted individual.

Figure 5:
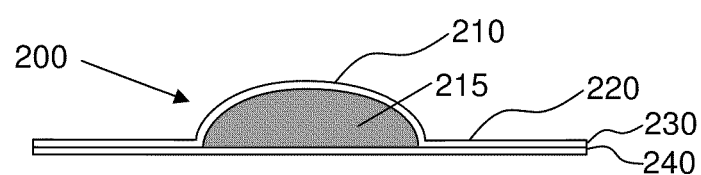
FIG. 5 shows a side-view schematic of one embodiment of a TMJ meniscus replacement device comprising an elliptical central core 200 a brim 220 encased in a sheath 230 and 240 covering the particulate or gel 215 core 210 and extending into the brim 220.
Figure 6:
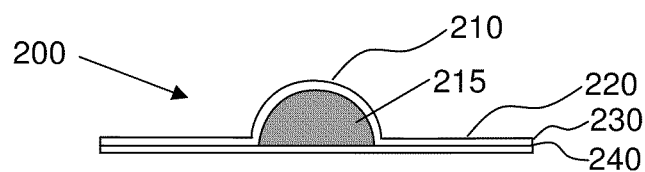
FIG. 6 shows a side-view schematic of one embodiment of a TMJ meniscus replacement device comprising a circular central core 200 a brim 220 encased in a sheath 230 and 240 covering the particulate or gel 215 core 210 and extending into the brim 220.

As shown in FIGS. 5 and 6, such a device 200 can comprise a central core 210 comprising particulate ECM powder or gel 215 which is encased in layers of laminar ECM 230 and 240 that extend from the core to form a brim 220. The particulate ECM can be any suitable size including, for example, particles with an average diameter of 10-400 µm, 1-500 µm, 1-700 µm, or any other suitable diameter. In accordance, average particle diameters include those with diameters of 50 µm, 100 µm, 150 µm, 200 µm, 250 µm and others include those with a diameter of 158 µm and 191 for example. Moreover the shape of the core can be concave, convex as shown in FIGS. 5 and 6, bi-concave (as in the original TMJ meniscus), bi-convex, or any combination thereof.

Independent of the particle size, in certain embodiments the device comprises a sheath which forms the brim as well as the encapsulation of the core. As such, the sheath can comprise one or more layers of laminar ECM. For example, the device can comprise 1, 2, 3, 4, 5, 6, 7, 8, 9, 10, 11, 12, 13, 14, 15, 16, 17, 18, 19, 20 or more layers. In certain embodiments, the layers themselves can substitute for the particulate matter. Thus, the disc itself can comprise 5, 10, 15, or 20 or more layers of laminar ECM encapsulated in a sheath of 1, 2, 3, 4, 5, 6, 7, 8, 9, 10, 11, 12, 13, 14, 15, 16, 17, 18, 19, 20 or more layers.

Those of skill in the art recognize that the diameter of the core and the width of the brim of a device described herein will depend on the anatomy of the individual. However, the height of the core can be between 0.5 and 4 cm, in certain instances. It is also contemplated that the core diameter can range from 8 to 12 mm, while the diameter of the entire device can range from 16 to 20 mm. The implant can be manufactured in a range of sizes. For example in certain embodiments small, medium, and large implants can be available depending on the patient's anatomy. For example and without limitation, an implant can have a core diameter by total diameter of 8 mm×16 mm; 10 mm×18 mm; and 12 mm×20 mm, respectively. The brim can be trimmed using scissors at the time of surgery to provide an optimal fit. The physical properties of the device can be such that the size and shape change as a function of the mechanical loads placed upon the device during movement of the adjacent body parts.

The biodegradable scaffolds may be porous. Porosity may be accomplished by a variety of methods. Although the biodegradable scaffolds may be porous or non-porous, it is often advantageous to use a process that produces a porous elastomeric scaffold. Non-limiting examples of such processes include solvent casting/salt leaching, electrodeposition, and thermally induced phase separation. In other examples, porosity may be accomplished by creating a mesh of fibers, such as by the aforementioned electrodeposition or by any suitable method of producing a woven or non-woven fiber matrix. As used herein, the term "porosity" refers to a ratio between a volume of all the pores within the polymer composition and a volume of the whole polymer composition. For instance, a polymer composition with porosity of 85% would have 85% of its volume containing pores and 15% of its volume containing the polymer. In certain non-limiting embodiments, the porosity of the scaffold is at least 60%, 65%, 70%, 75%, 80%, 85%, or 90%, or increments therebetween. In another non-limiting embodiment, the average pore size of the scaffold is between 0.1 and 300 microns, including increments therebetween. For example and without limitation, a biodegradable scaffold that acts as a barrier to bacteria and other pathogens may have an average pore size of less than 0.5 microns or less than 0.2 microns. When the scaffold is to be manufactured by electrodeposition, it is often advantageous to adjust the pore size or degree of porosity by varying the polymer concentration of the electrodeposition solution or by varying the spinning distance from the nozzle to the target. For example and without limitation, the average pore size may be increased by increasing the amount of polymeric components within the suspension used for electrodeposition, which results in larger fiber diameters and therefore larger pore sizes. In another non-limiting example, the average pore size can be increased by increasing spinning distance from the nozzle to the target, which results in less adherence between fibers and a looser matrix.

In certain non-limiting embodiments, the biodegradable scaffold is made by using solvent casting and salt leaching. This method involves dissolving the polymeric components that constitute the scaffold into a suitable organic solvent and then casting the solution into a mold containing small particles of predetermined size (known as porogens). Examples of suitable porogens include inorganic salts, crystals of saccharose, gelatin spheres or paraffin spheres. By adjusting the porogen size and/or the ratio of porogen to solvent, the porosity of the final elastomeric scaffold may be adjusted. After casting, the solvent is evaporated, and the resulting polymer composition is immersed into a second solvent that dissolves the porogen, but not the polymer, to produce a porous, sheet-like structure.

In other non-limiting embodiments, electrodeposition is used to fabricate the scaffold. The process of electrodeposition involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrodeposition, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target.

The properties of the electrodeposited scaffolds can be tailored by varying the electrodeposition conditions. For example, when the biased target is relatively close to the orifice, the resulting electrodeposited mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain non-limiting embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other non-limiting embodiments, the biased target is moved randomly relative to the orifice, so that the resistance to strain in the plane of the non-woven mesh is isotropic. The properties of the electrodeposited elastomeric scaffold may also be varied by changing the magnitude of the voltages applied to the electrodeposition system. In one non-limiting embodiment, the electrodeposition apparatus includes an orifice biased to 12 kV, a target biased to −7 kV, and a focusing ring biased to 3 kV. Moreover, a useful orifice diameter is 0.047" (I.D.) and a useful target distance is about 23 cm. Other electrodeposition conditions that can be varied include, for example and without limitation, the feed rate of the polymer solutions, the solution concentrations, and the polymer molecular weight. Non-limiting examples of useful range of high-voltage to be applied to the polymer suspension is from 0.5 to 30 kV, from 5 to 25 kV, and from 10 to 15 kV.

In another non-limiting embodiment, thermally induced phase separation (TIPS) is used to fabricate the biodegradable elastomeric scaffold. This method involves dispersing the polymeric components in a solvent (for example and without limitation, DMSO—dimethyl sulfoxide) and then casting, for example by injecting or otherwise placing the composition into a mold. The mold can have any useful shape, such as a sheet or net. In a typical TIPS fabrication process, a preformed mold is cooled to low temperature (for example and without limitation −80° C.), which causes the polymeric components to separate out of the solvent. The mold is then transferred to ethanol to extract the DMSO.

Fabrication and modification of the scaffold can comprise multiple steps using multiple techniques using polymer compositions that are the same or different. In one non-limiting example, TIPS is used to fabricate the scaffold and electrodeposition is used to form a fiber coating onto or around the scaffold. In another non-limiting example, solvent casting/salt leaching is used to fabricate the scaffold and electrodeposition is used to form a fiber coating onto or around the scaffold. The electrodeposition solution can contain one or more of any polymeric components, including synthetic polymeric components, biological polymeric components, or mixtures of both. The fiber coating formed by electrodeposition can be coated onto or around the entire scaffold or portions of the scaffold.

After fabricating the scaffold, the planar or three-dimensional surface of the scaffold may be functionally modified (functionalized) for any purpose, such as, without limitation, to promote cellular adhesion and migration onto and/or into the scaffold. In one non-limiting example, the surface is first treated to introduce a reactive group on the surface by any useful process, such as one of the many processes known in the art. Second, the activated surface is reacted with an adhesion-promoting peptide or group. The reactive group on the surface can be, for example and without limitation, a hydroxyl group or an amine group. In one embodiment, radio-frequency glow discharge is used to produce plasma containing ammonia gas and amine groups are introduced to the surface by treatment with the plasma. In another embodiment, radio-frequency glow discharge is used to introduce hydroxyl groups to the surface by treatment with plasma.

The activated surface can be modified with an adhesion-promoting oligopeptide to promote cellular ingrowth into and/or onto the scaffold. Non-limiting examples of adhesion-promoting oligopeptides include: RGD or RGDS (SEQ ID NO.: 1), a recognition site for fibronectin, vitronectin, fibrinogen, von Willebrand factor, and collagen; LDV, REDV (SEQ ID NO.: 2), PHSRN (SEQ ID NO.: 3), and KNEED (SEQ ID NO.: 4), which are recognition sites for fibronectin; YIGSR (SEQ ID NO.: 5) and IKVAV (SEQ ID NO.: 6), which are recognition sites for laminin; and DGEA (SEQ ID NO.: 7), a recognition site for collagen.

In one specific non-limiting embodiment, the scaffold is functionalized to present the peptide RGDS (SEQ ID NO.: 1) on its surface. First, the surface is treated with radio-frequency glow discharge containing ammonia gas to introduce amine groups. Ammonia-containing gas is generated by connecting a flask containing ammonium hydroxide (30 wt % solution) to the glow discharge reactor and maintaining pressure at $3\times10^{-3}$ Torr. The surface is further treated with 1,4-diisocyanatobutane to provide a reactive isocyanate group. Next, RGDS (SEQ ID NO.: 1) is attached to the activated surface. The activated surface is immersed in a solution of 20 µg/mL RGDS (SEQ ID NO.: 1) in PBS for 10 hours and then rinsed with PBS.

One or more of therapeutic agents can be introduced into the scaffold by any useful method, such as, without limitation absorption, adsorption, deposition, admixture with a polymer composition used to manufacture the scaffold and linkage of the agent to a component of the scaffold. In one non-limiting example, the therapeutic agent is introduced into a backbone of a polymer used in the scaffold. By adding the therapeutic agent to the polymer itself, the rate of release of the therapeutic agent may be controlled by the rate of polymer degradation. In another non-limiting example, the therapeutic agent is introduced when the scaffold is being made. For instance, during a solvent casting or TIPS process, the therapeutic agent can be added to the solvent with the polymer in the pre-formed mold. During an electrodeposition process, the therapeutic agent can be electrosprayed onto the polymer being spun. In yet another non-limiting example, the therapeutic agent is introduced into the scaffold after the device is made. For instance, the scaffold may be "loaded" with therapeutic agent(s) by using static methods. For instance, the scaffold can be immersed into a solution containing the therapeutic agent, permitting the agent to absorb into and/or adsorb onto the scaffold. The scaffold may also be loaded by using dynamic methods. For instance, a solution containing the therapeutic agent can be perfused or electrodeposited into the scaffold. In another instance, a therapeutic agent can be added to the scaffold before it is implanted in the patient.

Therapeutic agents within the scaffold can be used in any number of ways. In one non-limiting embodiment, a therapeutic agent is released from the scaffold. For example and without limitation, anti-inflammatory drugs are released from the scaffold to decrease an immune response. In another non-limiting embodiment, a therapeutic agent is intended to substantially remain within the scaffold. For example and without limitation, chemoattractants are maintained within the scaffold to promote cellular migration and/or cellular infiltration into the scaffold.

In one non-limiting embodiment, the scaffolds release therapeutic agents when the polymeric components degrade within the patient's body. For example and without limitation, the individual building blocks of the polymers may be chosen such that the building blocks themselves provide a therapeutic benefit when released in situ through the degradation process. In one non-limiting embodiment, one of the polymer building blocks is putrescine, which has been implicated as a substance that causes cell growth and cell differentiation.

In another non-limiting embodiment, at least one therapeutic agent is added to the scaffold before it is implanted in the patient. Generally, the therapeutic agents include any substance that can be coated on, embedded into, absorbed into, adsorbed onto, or otherwise attached to or incorporated onto or into the scaffold that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a scaffold comprising neurotrophic agents or cells that express neurotrophic agents may be applied to a wound that is near a critical region of the central nervous system, such as the spine. Alternatively, the therapeutic agent may be blended with the polymer while the polymer is being processed. For example, the therapeutic agent may be dissolved in a solvent (e.g., DMSO) and added to the polymer blend during processing. In another embodiment, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors cc and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

Methods of promoting wound healing or tissue generation or regeneration in a patient also are provided. The methods comprise, without limitation, implanting a scaffold as described herein at or near a site for wound healing or tissue generation or regeneration in the patient. In any such method, the scaffold may comprise a therapeutic agent as described herein.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, a NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In certain non-limiting embodiments, the therapeutic agent comprises cells that are added to the scaffold before or at the time of implantation. In such embodiments, it is often advantageous to use a porous biodegradable elastomeric scaffold, so that the cells may be incorporated into the porous structure of the scaffold (a condition referred to as "microintegration"). In this way, most of the cells will have a tendency to be trapped or otherwise contained within the porous structure of the scaffold. The cells that are microintegrated may remain after the scaffold has fully disintegrated within the patient. However, the microintegrated cells may also be merely cells that act as precursors to the final tissue that is formed when the scaffold has fully degraded.

Cells may be autologous (obtained from the patient to receive the scaffold), from an allogeneic or xenogeneic source or from any useful cell line, such as, without limitation, stem cells or precursor cells (cells that can differentiate into another cell type) that are capable of cellular growth, remodeling, and/or differentiation. By way of example only, the cells that may be incorporated onto or into the scaffold include stem cells, precursor cells, smooth muscle cells, skeletal myoblasts, myocardial cells, endothelial cells, fibroblasts, chondrocytes and genetically modified cells. Various commercially available cell lines include Clonetics® Primary Cell Systems (Lonza Group, Inc., Switzerland), ATCC.

Cells may be microintegrated with the scaffold using a variety of methods. For example and without limitation, the scaffold may be submersed in an appropriate growth medium for the cells of interest, and then exposed to the cells. The cells are allowed to proliferate on the surface and interstices of the scaffold. The scaffold is then removed from the growth medium, washed if necessary, and implanted. Alternatively, the cells may be placed in a suitable buffer or liquid growth medium and drawn through the scaffold by using vacuum filtration. In another non-limiting embodiment, the cells of interest are dissolved into an appropriate solution (e.g., a growth medium or buffer) and then sprayed onto a scaffold while the scaffold is being formed by electrodeposition. In yet another non-limiting embodiment, the cells are placed in a solution that is biased and then electrosprayed onto the scaffold while it is being electrodeposited. By way of example only, the cells that may be incorporated on or into the scaffold include chondrocytes, stem cells, precursor cells, smooth muscle cells, skeletal myoblasts, myocardial cells, endothelial cells, fibroblasts and genetically modified cells.

In one non-limiting embodiment, the genetically modified cells are capable of expressing a therapeutic substance, such as a growth factor. Cells can be modified by any useful method in the art. For example and without limitation, the therapeutic agent is a growth factor that is released by cells transfected with cDNA encoding for the growth factor. Therapeutic agents that can be released from cells include, without limitation, a neurotrophic factor, such as nerve growth factor, brain-derived neurotrophic factor, neurotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2); an anti-inflammatory cytokine; and an anti-inflammatory protein. The cells may be autologous, allogeneic, etc.

In addition to providing scaffolds as described above, methods of using such elastomeric scaffolds are encompassed herein. Generally, a scaffold can be implanted by using any suitable medical procedure that facilitates use of the scaffold to provide a therapeutic benefit. As used herein, the terms "implanted" and "implantation" and like terms refer to an act of delivering a scaffold or scaffold-containing device to a site within the patient and of affixing the scaffold or device to the site. The site of implantation in a patient typically is "at or near a site for wound healing or tissue generation or regeneration in the patient," meaning the scaffold-containing device is implanted in, on, onto, adjacent to or in proximity to a desired site of delivery to facilitate healing and/or tissue generation or regeneration to repair an injury or defect in the patient and/or to achieve a desired effect in the patient, such as wound drainage. The delivery method may also include minimally invasive methods such as by catheter based technology or by needle injection. The patient may be human or animal. The scaffold may be delivered by any surgical procedure, including minimally invasive techniques, such as laparoscopic surgery, as well as invasive techniques such as thoracic surgery and fasciotomy. The scaffold or device may be implanted alone or implanted in conjunction with surgical fasteners, such as sutures, staples, adhesives, screws, pins, and the like. Additionally, biocompatible adhesives, such as, without limitation, fibrin-based glue) may be used to fasten the scaffolds as well.

In yet another non-limiting embodiment, the scaffold can be in the form of a powder or fine particles (for example, formed by shredding a non-woven mesh formed by electrodeposition or TIPS). In these situations, it may be advantageous to derivatize the elastomeric scaffold with therapeutic agents, such as antibiotics or growth factors, prior to insertion into the wound.

Example 1

Preparation of Powdered Extracellular Matrix from Porcine Urinary Bladders (UBM)

Porcine urinary bladders were harvested from pigs immediately following euthanasia. Connective tissue and adipose tissue were removed from the serosal surface and any residual urine was removed by repeated washes with tap water. The tunica serosa, tunica mucosa externa, the tunica submucosa, and most of the tunica muscularis interna were mechanically removed and the luminal urothelial cells of the basement membrane were dissociated by soaking in 1.0 N saline solution yielding a biomaterial composed primarily or exclusively of the basement membrane plus the subjacent tunica propria. This bi-laminate structure was referred to as urinary bladder matrix (UBM). UBM sheets were disinfected for two hours on a shaker in a solution containing 0.1% (v/v) peracetic acid, 4% (v/v) ethanol, and 95.9% (v/v) sterile water. The peracetic acid residue was removed by washing with sterile phosphate-buffered saline (pH=7.4) twice for 15 minutes each and twice for 15 minutes each with sterile water. UBM sheets were lyophilized and then chopped into small sheets for immersion in liquid nitrogen. The snap frozen material was then reduced to small pieces with a WARING™ blender so that the particles were small enough to be placed in a rotary knife mill. A #60 screen was used to restrict the collected powder size to less than 250 mm. Sonic sifting and laser diffraction were used to analyze the particle size distribution that resulted from the powdering methods as described in Gilbert et al., Biomaterials 26 (2005) 1431-1435, herein incorporated by reference in its entirety. The particles formed were irregularly shaped and could be defined generally as sheet-like or fiber-like.

In another method, the ECM was first soaked in the disinfected material in a 30% (w/v) NaCl solution for 5 min. The material was then snap frozen in liquid nitrogen to precipitate salt crystals, and lyophilized to remove residual water. This material was then comminuted as described supra. By precipitating NaCl within the tissue, it was expected that the embedded salt crystals would cause the material to fracture into more uniformly sized particles. The particles were suspended in deionized water and centrifuged for 5 min at 1000 rpm three times to remove the NaCl. The suspension was snap frozen and lyophilized again. Finally, the powder was placed in a rotary knife mill to disaggregate the individual particles. Sonic sifting and laser diffraction were used to analyze the particle size distribution that resulted from the two powdering methods. Sonic sifting involved separating the powder by size through a series of graduated screens stacked in a vertical configuration. The powder passed through the screens as a result of sonic pulses along the longitudinal axis of the stack and mechanical agitation in the plane of the screens. The screen sizes used were 212, 125, 90, 63, and 38 mm. The mass of the powder from each cut was weighed and the amount of material in each cut was represented as the percentage of the total mass. This data was converted to a percentage of the total volume based on an assumption that the density of the material was the same for the two production methods.

The ultrastructure for particles produced by the first method was evaluated with SEM. The particles formed by the first method were irregularly shaped and could be defined generally as sheet-like or fiber-like. Examination of the particles at higher magnification (500×) showed that two distinct surface ultrastructures were present. One surface appeared to be quite smooth while the other appeared to be more fibrous. Since sonic sifting did not give an accurate description of the particle size distribution, only laser diffraction was used to analyze the size of the UBM powder produced by the salt precipitation method. The mean particle size was found to be smaller for powder produced by the salt precipitation method than the particle size produced by the first method. Furthermore, the size of the particles was more uniform when produced by the salt precipitation method. The particles formed after salt precipitation showed a different morphology than those formed by the first method as shown with SEM. The larger particles in the distribution (150-200 µm) appeared to have porous surfaces and there was a large population of very fine particles (approximately 1 µm) which tended to associate with the larger particles or agglomerate.

Example 2

Manufacture of a TMJ Meniscus Replacement Device

Laminar ECM was layered into a pressure mold device. Urinary bladder matrix (UBM) sheets were prepared as described in Example 1 above. After undergoing a decellularization step, hydrated sheets of UBM were cut and placed, with the luminal surface facing the mold, onto a pressure mold device. In various embodiments, anywhere from 1 to about 20 layers of UBM were used to create the device. The mold consisted of a block of hard plastic that has been milled to create a depression in the center with the approximate size of the desired central core (see e.g., 110 of FIGS. 3 and 4) of the TMJ device.

Figure 9A:
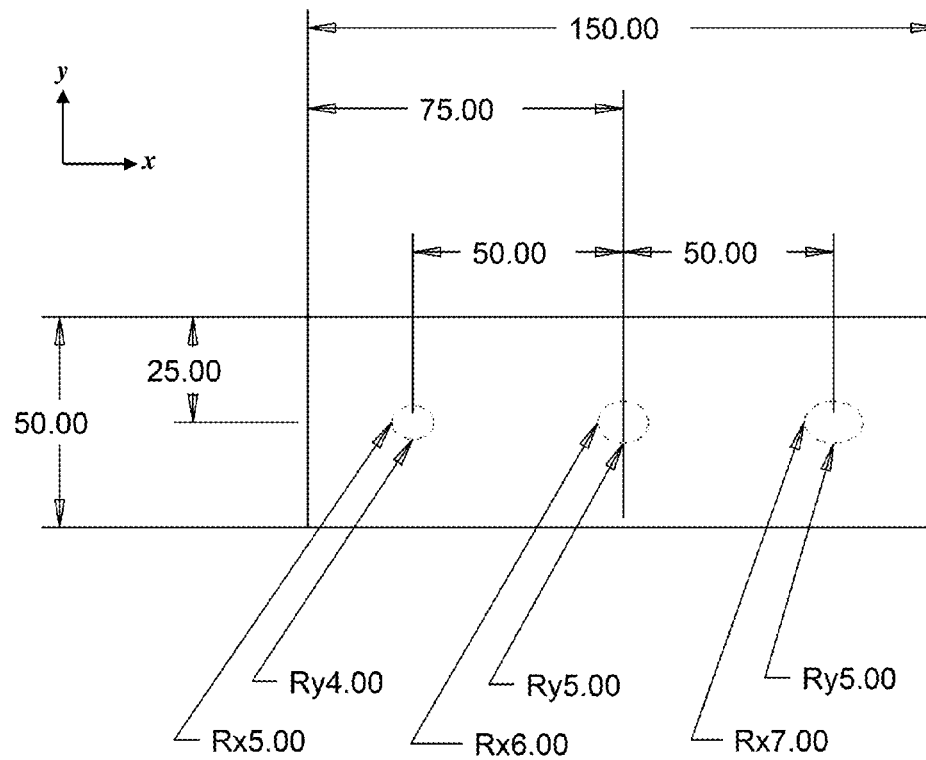
FIG. 9A shows a top-view of the mold.
Figure 9B:
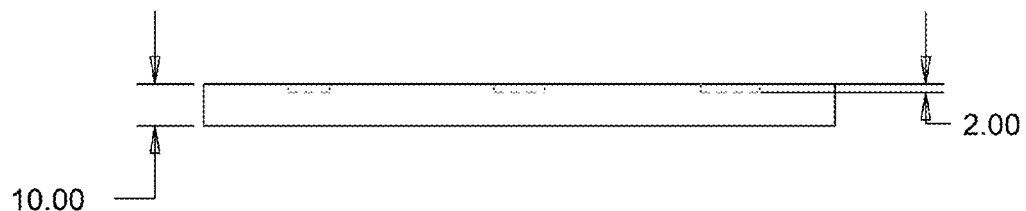
FIG. 9B shows a side-view of the mold along the x-axis.
Figure 9C:
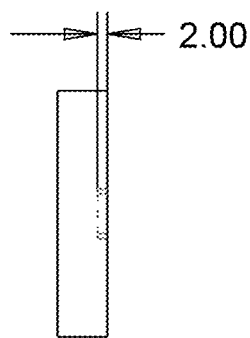
FIG. 9C shows a side-view of the mold along the y-axis.
Figure 10A:
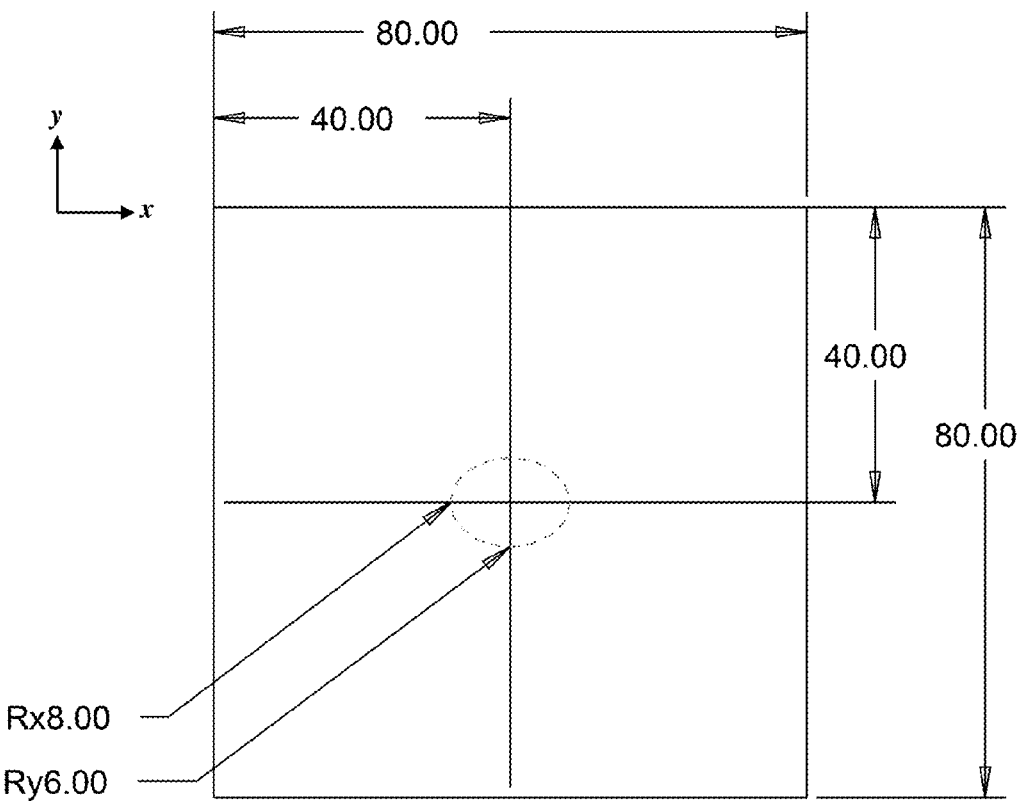
FIG. 10A shows a top-view of the mold.
Figure 10B:
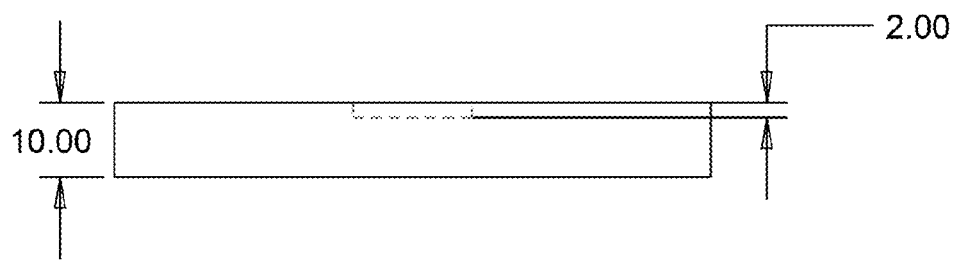
FIG. 10B shows a side-view of the mold along the x-axis.
Figure 10C:
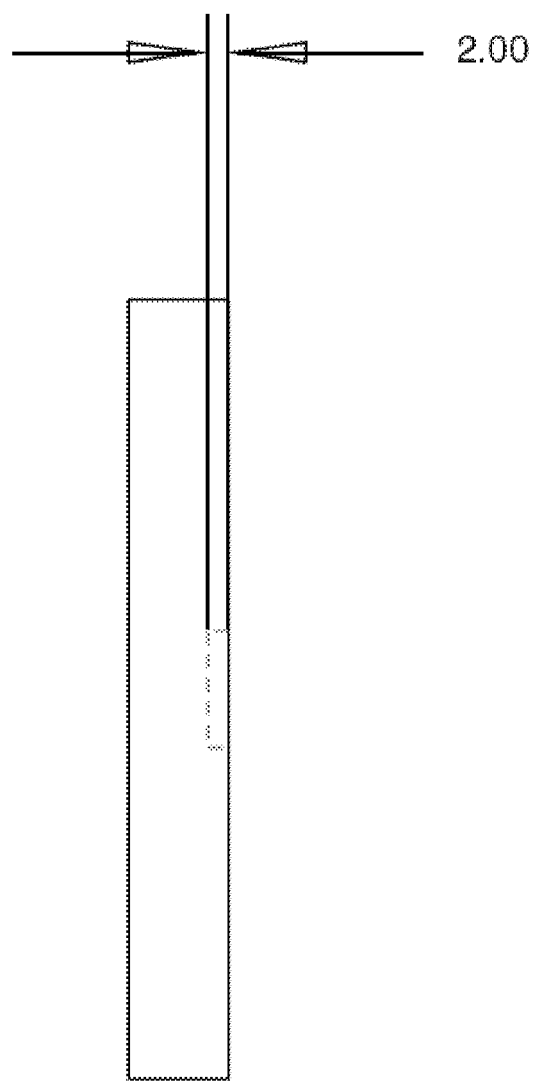
FIG. 10C shows a side-view of the mold along the y-axis.

Non-limiting examples of molds include FIG. 9, which shows a schematic of a mold for a canine TMJ meniscus replacement device, and FIG. 10, which shows a mold for a human TMJ meniscus replacement device. Dimensions are shown in millimeters (mm).

Following placement of the sheet form of the UBM (or any other ECM), the sheets are pressed such that they will line the inside of the depression, creating a pocket where the particulate ECM (or gel, or multiple layers of the sheet form) will be placed. Particulate ECM powder manufactured as in Example 1 was then used to fill the void in the mold. Notably, any particulate or gel or sheets could be packed into the pocket until the desired fill is achieved (e.g., ~200 mg of powder in the canine devices). Additional layers of laminar ECM were then placed over the mold.

Figure 7:
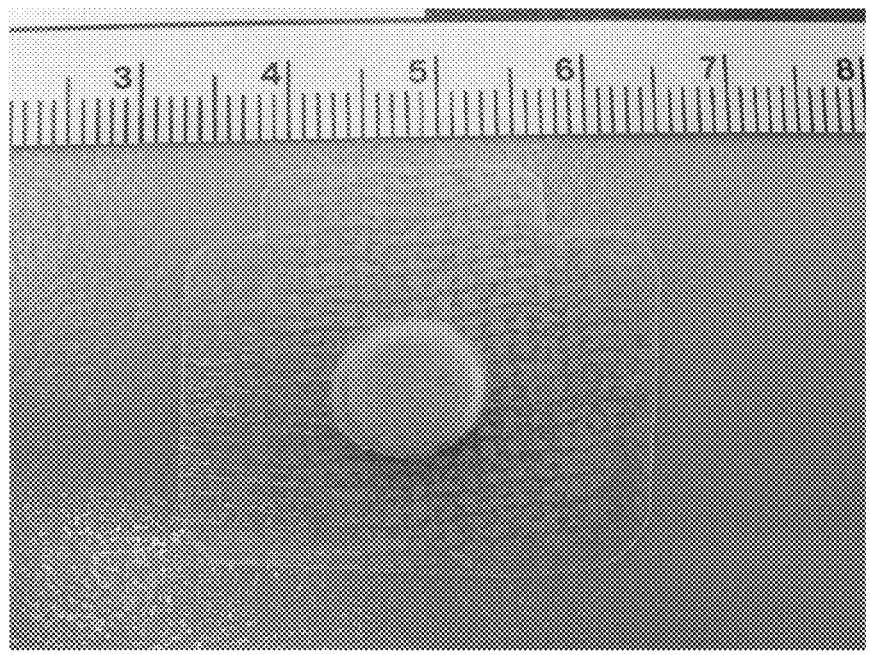
FIG. 7 is a photograph of one embodiment of a TMJ meniscus replacement device prior to implantation.
Figure 8:
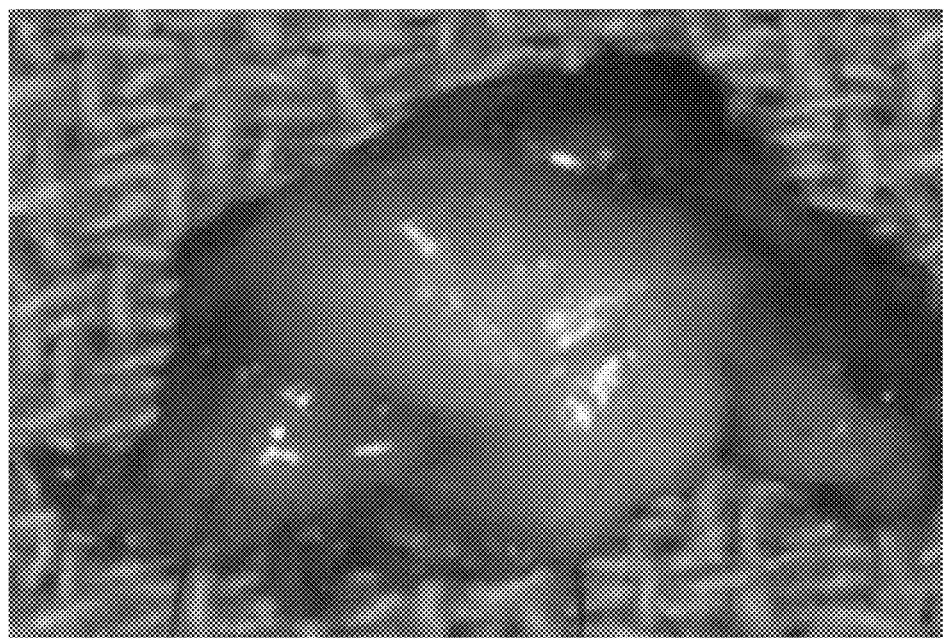
FIG. 8 is a photograph of one embodiment of a TMJ meniscus replacement device after two months of implantation. Notably, cellular influx and vascularization of the core has occurred, indicating the body has begun to actively remodel the device.

More ECM sheets were then cut to size and placed over top of the previously placed sheets and powder core to create an enclosed core of ECM powder. Again, the number of sheets placed can range from 1 to about 20 layers. The mold, sheet, powder, sheet construct were then covered with cheese cloth and a piece of metal mesh and sealed inside of a plastic pouch for vacuum pressing. The device was then pressed using a vacuum pump with a condensate trap inline. The constructs were subjected to a vacuum of at least 28 inches Hg until dried, leaving a multilaminate construct. (See FIG. 7).

Example 3

Canine Model for TMJ Meniscus Implantation

Five female mongrel dogs of approximately 15-20 kg (purchased from Marshall Bio-Resources USA (North Rose, N.Y.)) were subjected to unilateral meniscectomy followed by replacement of the meniscus with a UBM-ECM device. The UBM-ECM device consisted of particulate UBM-ECM encapsulated between sheets of UBM-ECM forming a "pillow-like" device. At time points of 3 weeks, 1, 2, 3, and 6 months, one animal was sacrificed and the condylar head, temporal fossa, and the UBM-ECM implant were excised and assessed using histologic and immunohistochemical methods.

UBM-ECM Device Preparation

UBM-ECM was prepared from porcine bladders. Briefly, urinary bladders were harvested from market weight pigs immediately following sacrifice. The bladder tissue was rinsed in water to facilitate the removal of excess urine and the urothelial cell layer. Excess connective and adipose tissue was removed from the serosal surface of the bladder using scissors. The apex of the bladder was removed and the bladder was then split longitudinally from the apical opening to the neck of the bladder forming a rectangular sheet. The tunica serosa, tunica muscularis externa, tunica submucosa, and the majority of the muscularis mucosa were removed by mechanical delamination of the abluminal side of the bladder. The remaining tissue consisted of the basement membrane, tunica propria, and resident cells.

The tissue was then treated in a 0.1% peracetic acid/4% ethanol solution for two hours to initiate decellularization and disinfect the tissue. Following treatment in the peracetic acid/ethanol solution, the tissue was repeatedly washed in phosphate buffered saline (PBS) and water to remove cellular remnants and traces of the peracetic acid/ethanol solution and to return the pH of the material to 7.4. The remaining decellularized tissue was stored in water until used and represented the hydrated sheet form of UBM-ECM. A portion of the hydrated sheet form of UBM-ECM was frozen and lyophilized. The dry sheet was cut into smaller pieces and comminuted using a Wiley mill with a #60 mesh screen. The comminuted UBM-ECM represented the particulate form of UBM-ECM.

A hard plastic mold was milled to create an oval-shaped depression with the approximate size of the desired central core of the TMJ device (10 mm×14 mm oval, 2 mm depth) and a flat surface surrounding the depression to allow for the formation of a "pillow-like" core and a flat anchoring site. Two hydrated sheets of UBM-ECM were then cut to size and placed onto the mold. Following placement, the hydrated sheets were pressed to line the inside of the depression, creating a pocket into which particulate UBM-ECM was packed. Approximately 200-300 mg of the ECM powder was packed into the depression and two hydrated sheets were cut to size and placed over the top of the powder to create an enclosed core. The constructs were subjected to a vacuum of at least 28 inches Hg until dry, forming a multilaminate construct. All constructs were terminally sterilized using ethylene oxide prior to implantation.

Surgical Procedure

All animals were sedated with acepromazine (01-0.5 mg/kg body weight) prior to intubation and maintenance of a surgical plane of anesthesia with isoflurane (1-5%). The surgical site was shaved and prepared using a betadine scrub prior to the placement of sterile drapes. An incision was made anterior to the tragus, preserving local innervation and vasculature. The native meniscus was then isolated and completely removed.

The UBM-ECM implants were hydrated in sterile saline for approximately 10 minutes prior to use as a replacement device for the native meniscus. Devices were placed such that the powder "pillow" was situated between the temporal fossa and the condylar head. Three holes were created in the temporal fossa and the implants were then secured to the temporal fossa with fixation sutures. Fixation sutures were also placed in the anterior and posterior aspects of the implant through the adjacent tissues, and soft tissue and the skin was then closed using resorbable suture material.

Post Operative Care

Following the surgical procedure, the animals were recovered from anesthesia, extubated and monitored until resting comfortably in a sternal position. The animals were then monitored and the following parameters were recorded every 3 hours for the first 24 hours post surgery: pulse rate, strength of pulse, capillary refill time, respiratory rate and ability to maintain an open airway, urinary output, and defecation. Body temperature was measured and recorded every 12 hours. The animals were restricted to confinement housing (not more than 2-3 days) until stable, and were then placed in 10×14 ft runs and allowed free movement. Buprenorphine was administered (0.005-0.01 mg/kg body weight) for 5 days post operatively and then as needed thereafter for pain management. The dogs were also given Cephalexin (35 mg/kg body weight) for 5 days post-operatively. Animals were fed a soft diet for the first 5-7 days post operatively and were returned to a normal hard diet thereafter.

Euthanasia and Sample Harvest

At the predetermined date of sacrifice, the animals were sedated with acepromazine (0.1-0.5 mg/kg body weight), anesthetized using isoflurane (5%) and euthanized by intravenous administration of pentobarbital sodium (390 mg/4.5 kg body weight). Following euthanasia, the temporal fossa, the condylar head, and the interpositional material between the structures were excised and fixed in 10% neutral buffered formalin for histologic and immunolabeling examination. Native fossa, condyle, and meniscus tissues were also harvested as controls and were treated in identical fashion as the experimental explant tissue.

Gross Morphologic Examination

At the time of explant, the joint space of all animals was examined for signs of pathologic degeneration of the articulating surfaces of the temporal fossa and mandibular condyle and/or other signs of pathologic joint inflammation.

Histologic Evaluation

Formalin fixed tissues were embedded in paraffin, cut into 6 µm sections and mounted on glass slides. Sections were deparaffinized by immersion in xylenes followed by a graded series of ethanol. The slides were stained using hematoxylin and eosin or Herovici's polychrome, and were then dehydrated in ethanol and xylenes prior to coverslipping. The slides were then evaluated under light microscopy. Pre-implant UBM-ECM devices were also subjected to histologic evaluation using the methods described above. Additionally, pre-implant UBM-ECM scaffolds were stained with 4',6-diamidino-2-phenylindole (DAPI) to confirm complete decellularization.

Immunolabeling Studies

Sections of the TMJ meniscus tissue were labeled using antibodies specific for CD31 and CD68 to determine the presence of blood vessels and macrophages, respectively, within the remodeling UBM-ECM implant. Slides were deparaffinized by immersion in xylenes and a graded series of ethanol. Antigen retrieval was then performed by boiling slides in 10 mM citric acid monohydrate (pH 6.0) for 20 minutes. Following antigen retrieval, the slides were exposed to a solution consisting of TRIS buffered saline and 0.05% Tween 20. Slides were then washed in PBS three times for a total of 10 minutes and a solution of 3% $H_2O_2$ in methanol was applied for 30 minutes at room temperature to quench endogenous peroxidase activity. Slides were blocked in a solution consisting of 2% normal serum, 1% BSA, 0.1% Triton-X 100, and 0.05% Tween 20 in PBS for 30 minutes at room temperature. Primary antibodies were diluted in the blocking solution (1:250) and applied to the slides overnight at 4° C. Slides were washed in PBS, and secondary antibodies diluted in blocking solution were applied for 30 minutes at room temperature. Slides were washed in PBS and ABC reagent (Vector, Burlingame, Calif.) was applied to for 30 minutes at 37° C. The slides were washed in PBS and water prior to development using 4% diaminobenzadine substrate (Vector) solution. Finally, slides were counterstained using hematoxylin (Vector), dehydrated using the reverse of the dewaxing procedure above, and coverslipped for examination under light microscopy.

Results

All of the animals in this study survived the surgical procedure and lived until their predetermined sacrifice date without complication.

Gross Morphologic Findings

Gross morphologic examination showed that there was little to no change in the articulating surfaces of the temporal fossa or the mandibular condyle at any time point following placement of the UBM-ECM device. There were no signs of synovitis, or excess fluid in the joint space. The UBM-ECM device showed progressive remodeling and was replaced with a structure that highly resembled the fibrocartilage of the native TMJ disk by the 6 month post surgical time point. It was not possible to differentiate the original UBM-ECM device from newly deposited host tissue at any of the time points investigated in this study.

Histopathologic Findings

Histologic evaluation was performed both at the center of the remodeling implant and at the periphery of the implant to determine both the bulk morphology of the remodeling device and the degree of integration of the device with the muscular tissues at the peripheral attachment sites.

Pre-Implantation UBM-ECM Device

Histologic staining of the UBM-ECM device showed small particles of mature, well-organized collagenous extracellular matrix (UBM-ECM powder) encapsulated within sheets of the same. The particles were randomly oriented and the internal structure of the device was highly porous. The exterior surface of the device was also observed to be composed of mature, well-organized collagenous extracellular matrix and was characterized by its smooth, dense structure (UBM-ECM sheets).

Remodeled UBM-ECM Device

Bulk Morphology

At three weeks the implanted UBM-ECM device was no longer identifiable and the site of remodeling was characterized by a dense infiltration of predominantly mononuclear cells within newly deposited ECM. Herovici staining showed that the newly deposited ECM was composed of both collagen type I and small amounts of collagen type III.

At one month the site of remodeling was characterized by a dense, randomly distributed cellular infiltrate consisting of both mononuclear cells and spindle shaped cells. There was a decrease in the number of mononuclear cells compared to the three week time point. Herovici staining indicated that the remodeling site contained both collagen type I and small amounts of collagen type III with an increase in both the density and the degree of organization of the newly deposited collagen type I.

At two months the site of remodeling was characterized by an increase in the number of spindle shaped cells within the remodeling site with a concomitant decrease in the number of mononuclear cells and a decrease in overall cellular density compared to earlier time points. Herovici staining indicated that the remodeling site contained both collagen type I and collagen type III with a predominance of collagen type I. It was also noted that the organization of the collagen was increased with a morphology that more resembled the native TMJ than did the collagen deposited in the remodeling site at the three week or one month time points.

At three months the density of the cellular infiltrate within the site of remodeling was greatly decreased compared to all earlier time points. The cellular population at the three month time point was characterized by predominantly spindle shaped cells with a small number of randomly distributed mononuclear cells remaining within the remodeling site. Herovici staining showed that, as at previous time points, the remodeling site was characterized by a deposition of both collagen type I and collagen type III with a predominance of collagen type I at the three month time point. The density of the collagen type I deposited in the remodeling site was greater than any of the previous time points, and the morphology of the collagen matrix present in the remodeling site at three months highly resembled that of the native TMJ.

At six months the remodeling site was characterized by a sparse population of spindle shaped cells within an aligned matrix of collagenous tissue. Herovici staining indicated that there were highly organized collagen type I fibers formed within the remodeling site with interspersed collagen type III fibrils. The morphology of the remodeled tissue at 6 months was almost indistinguishable from that of the native TMJ.

B. Peripheral Musculature Attachment Site

Histologic staining showed that the newly deposited ECM within the site of remodeling was well integrated with the native musculature at the periphery of the implanted device as early as one month post-implantation. A dense population of small, dark staining cells was observed adjacent to bundles of skeletal muscle at the interface between the remodeling UBM-ECM device and native host tissue at one month post implantation. The degree of integration of the UBM-ECM device with the native host tissue was shown to increase with time and ingrowth of host skeletal muscle tissue into the site of remodeling was observed. By six months post-implantation, bundles of skeletal muscle were observed within the site of remodeling and were surrounded by mature, well-organized collagenous extracellular matrix. Muscular ingrowth was observed only at the periphery, and not in the bulk, of the remodeling UBM-ECM device.

Articulating Surfaces

Macroscopic and histologic examination showed that there were no pathologic changes in the articulating surfaces of the condyle or the fossa at any of the time points investigated in this study. That is, the articulating surfaces of the fossa and condyle were characterized by the presence of smooth, thin fibrocartilagenous tissue which resembled that observed in the contralateral control at all of the time points examined in this study.

Immunolabeling Findings

CD31

Immunolabeling for CD31 showed that there were a large number of randomly distributed blood vessels within the site of remodeling at early time points (3 weeks and 1 month). Both the number and size of the vessels were shown to decrease by 3 months post implantation. The number and size of the vessels within the remodeling UBM-ECM device were further decreased by 6 moths post implantation and resembled the vasculature found within the native TMJ meniscus. Both the number and the size of the vessels observed were greater at the periphery of the device than in the bulk at all time points investigated.

B. CD68

Immunohistochemical staining for CD68 showed that a large number of mononuclear macrophages were present within the dense cellular infiltrate that was observed during the histologic evaluation of tissue 3 weeks, 1 month, and 2 months post implantation. The number of CD68+ macrophages decreased with time and few, if any, mononuclear cells were observed by 3 months post implantation. By 6 months post implantation, the dense mononuclear macrophage population observed at early time points was been replaced by a population of spindle shaped CD68− cells resembling those found in the native TMJ meniscus. It should be noted that the temporal and spatial patterns of the macrophage infiltration seen in this study are the same those observed in numerous other studies utilizing acellular ECM scaffold materials for tissue reconstruction.

Summary

These results show that the UBM-ECM device acted as an inductive template for constructive remodeling of the TMJ meniscus following meniscectomy. The remodeling of the UBM-ECM device was characterized by infiltration of a cell population consisting predominantly of mononuclear macrophages accompanied by rapid degradation of the scaffold material, deposition of new host-derived tissue, and angiogenesis at early time points changing to a sparse population of spindle shaped cells and small blood vessels within mature, highly aligned collagen with time. By six months post implantation, the morphology of the remodeled ECM scaffold site highly resembled that of the native TMJ meniscus both in terms of its shape and size as well as its components, collagen fiber organization, and the makeup of the cell population. The remodeled tissue was shown to be well-integrated with the native musculature at the periphery of the implant and host derived muscle tissue was observed within the site of tissue remodeling. Further, implantation of the UBM-ECM device was not associated with any pathologic changes in the articulating surface of the fossa or condyle at any of the time points investigated.

Acellular, non-crosslinked ECM scaffolds are shown to induce the formation of new, site-appropriate, functional, host tissue that is arranged in a spatially appropriate pattern for the tissue of interest. This remodeling process is in direct contrast to the default mechanism of mammalian tissue repair following injury, which generally results in inflammation and scarring with no functional recovery. The exact mechanisms by which this ECM mediated tissue specific constructive remodeling occurs are not fully understood; however, a number of factors including mechanical forces, scaffold degradation with concomitant release of bioactive ECM molecules and matricryptic peptides, and the ability of ECM scaffolds to modulate the host immune response are known to play important roles in determining remodeling outcomes.

This is the first report of an intact ECM scaffold material used in an in vivo study of meniscus replacement. The non-crosslinked UBM-ECM device used in the present study was rapidly degraded and was indistinguishable from newly deposited host tissue at the three week time point, indicating that scaffold degradation in the TMJ location occurs very rapidly in this anatomic site. This rapid degradation may be due, in part, to the highly complex synovial fluid milieu and the mechanical loading environment of the TMJ location compared to other locations in which ECM scaffolds have been previously implanted. The TMJ meniscus has been shown to experience large tensile, compressive, and shear forces during everyday motion. These large and diverse forces may have contributed to the rapid degradation of the UBM-ECM scaffold observed in this study. Further, these site-specific forces may have influenced the formation and resultant site appropriate spatial arrangement of fibrocartilage, vasculature, and muscle observed in this study.

Example 4

Evaluation of TMJ Regeneration at Six (6) Months

Follow-up studies were conducted in light of the results of Example 3. Ten (10) dogs were used in this study. Each dog served as its own control. All dogs had unilateral (left) and contralateral (right) meniscectomies of the TMJ meniscus. Contralateral TMJ menisci were replaced with the UBM scaffold described in Example 3. After 6 months necropsies were performed on the dogs. Menisci from four dogs have not yet been removed. The menisci were evaluated visually, and then histology, immunohistochemical staining, biochemical assays and biomechanical testing were performed.

At the time of explant, the joint space of all animals was examined for signs of pathologic degeneration of the articulating surfaces of the temporal fossa and mandibular condyle and/or other signs of pathologic joint inflammation. The UBM menisci also were examined. Gross morphologic examination showed that there was little to no change in the articulating surfaces of the temporal fossa or the mandibular condyle. There were no signs of synovitis, or excess fluid in the joint space. The UBM-ECM device was replaced with a structure that highly resembled the fibrocartilage of the native TMJ disk. It was not possible to differentiate the original UBM-ECM device from newly deposited host tissue.

Figure 11:
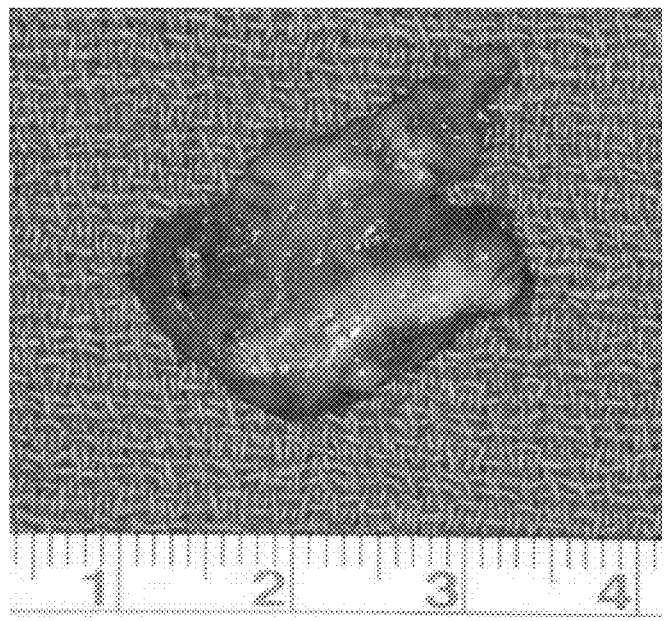
FIG. 11 is a photograph of the UBM meniscus in dog 1 described in Example 4 after six months.
Figures 12A, 12B:
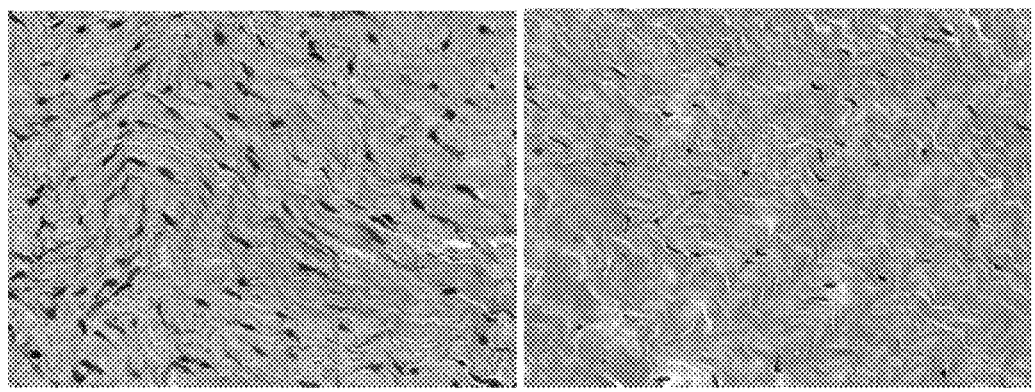
FIGS. 12A and 12B are photomicrographs of Hematoxylin and Eosin stains for the UBM meniscus for dogs 1 and 2 respectively.

For histological studies, the explanted tissue were sectioned (see FIG. 11) and slides were prepared and stained with Hematoxylin and Eosin as described above. FIGS. 12A and 12B show normal Hematoxylin and Eosin stains for the UBM meniscus for dogs 1 and 2 respectively, and is exemplary of the results obtained for other subject dogs.

Figure 13A:
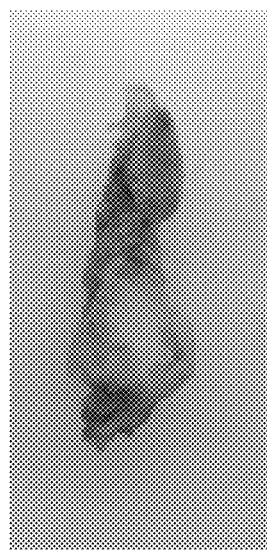
FIG. 13A is a photograph of a cross-section of the UBM meniscus from Dog 1 showing gross morphology.
Figure 13B:
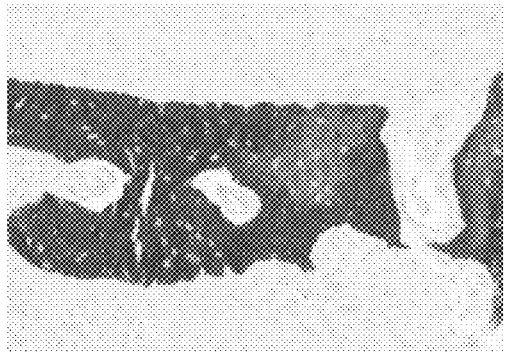
FIGS. 13B and 13C are photomicrographs (200×) showing the results of Von Kossa staining of sections of the UBM menisci from dogs 1 and 2.
Figure 13C:
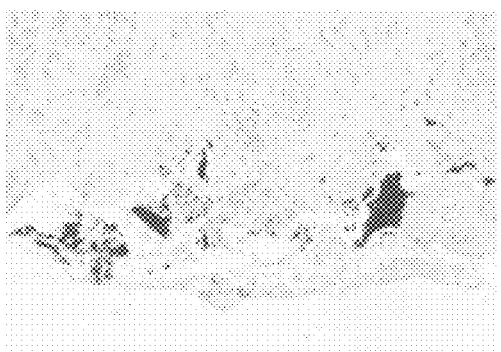

Von Kossa staining was performed on menisci of dogs 1 and 2. Briefly, paraffin sections are deparaffinized and hydrated with water; rinsed with distilled water; incubated with 1% silver nitrate solution and placed under ultraviolet light for 20 minutes; incubated with 5% sodium thiosulfate for 5 minutes to remove un-reacted silver; rinsed in distilled water; counterstained with nuclear fast red for 5 minutes; rinsed in distilled water; dehydrated in alcohol and xylene and a coverslip was applied. FIG. 13A shows gross morphology of the UBM meniscus from Dog 1, which shows some apparent mineralization. Other UBM menisci did not show evidence of mineralization to this extent, and most showed no evidence of mineralization. FIGS. 13B and 13C show the results of Von Kossa staining of sections of the UBM menisci from dogs 1 and 2, indicating that dog 1 had evidence of calcification, while dog 2 had little or no mineralization. Because the mineralization is found predominantly in one sample, it is believed that the UBM implantation method affects the character of the UBM menisci. Where mineralization is found it is believed bone progenitor cells contaminated the implant, and that care needs to be taken not to contaminate the implant with bone or other non-cartilage progenitor cells during implantation.

Figure 14A:
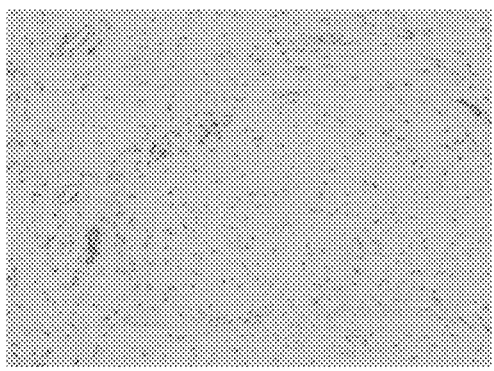
FIGS. 14A and 14B are photomicrographs (200×) showing CD31 staining for dogs 1 and 2, respectively.
Figure 14B:
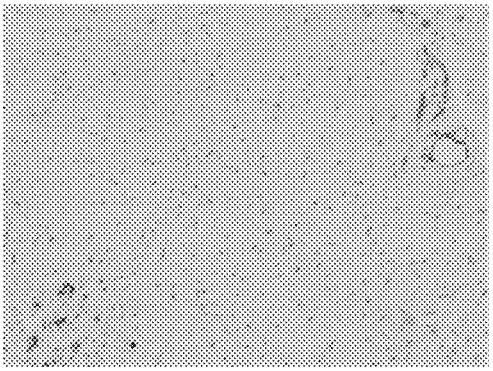
Figure 15A:
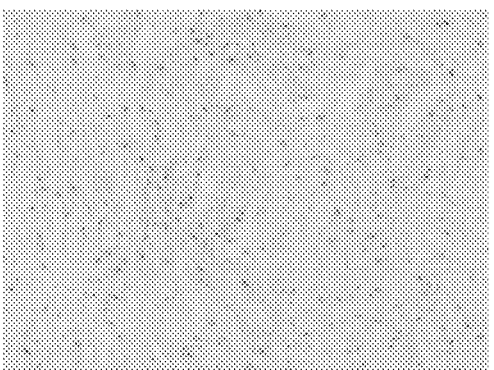
FIGS. 15A and 15B are photomicrographs (200×) showing CD68 staining for dogs 1 and 2, respectively.
Figure 15B:
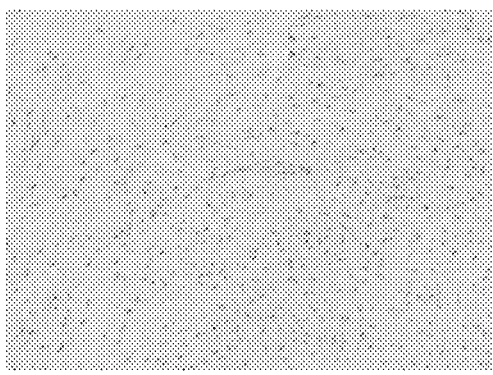

Immunohistochemical analysis of markers of blood vessels and macrophages (CD31 and CD68, respectively) was performed essentially as described in Example 3. FIGS. 14A and 14B show CD31 staining for dogs 1 and 2, respectively. FIGS. 15A and 15B show CD68 staining for dogs 1 and 2, respectively.

Biomechanical and Biochemical Analysis

Four millimeter (4 mm) cylindrical punches were made for each meniscus tested, leaving much of the tissue remaining for biochemical analysis. The cylindrical shape was chosen for simplicity of stress calculations and modeling. The samples were placed in a temperature-controlled saline (0.9%) bath prior to testing. All testing was performed at 37° C. using an MTS Insight testing system. Compression, relaxation and elastic modulus were analyzed as shown below.

Figure 16A:
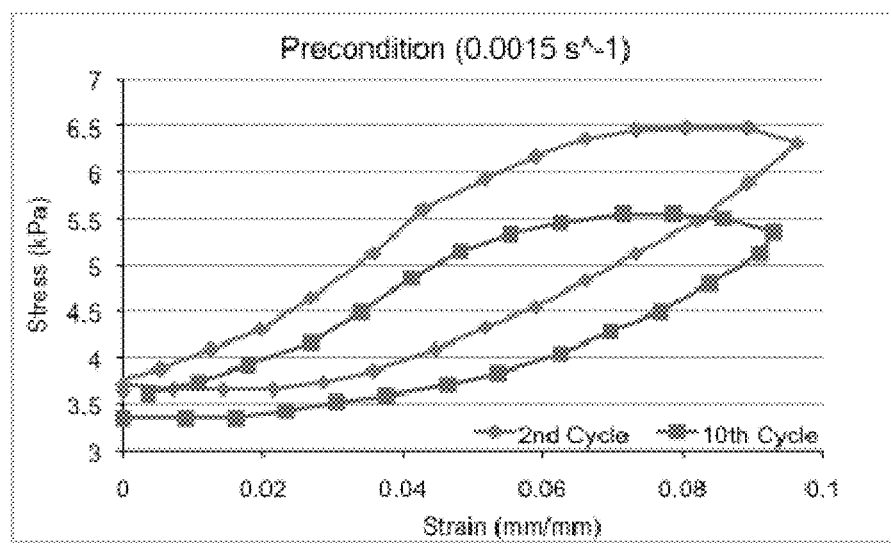
FIGS. 16A and 16B are graphs showing compressive behavior for a native canine TMJ disc and for a pre-implantation UBM construct, respectively.
Figure 16B:
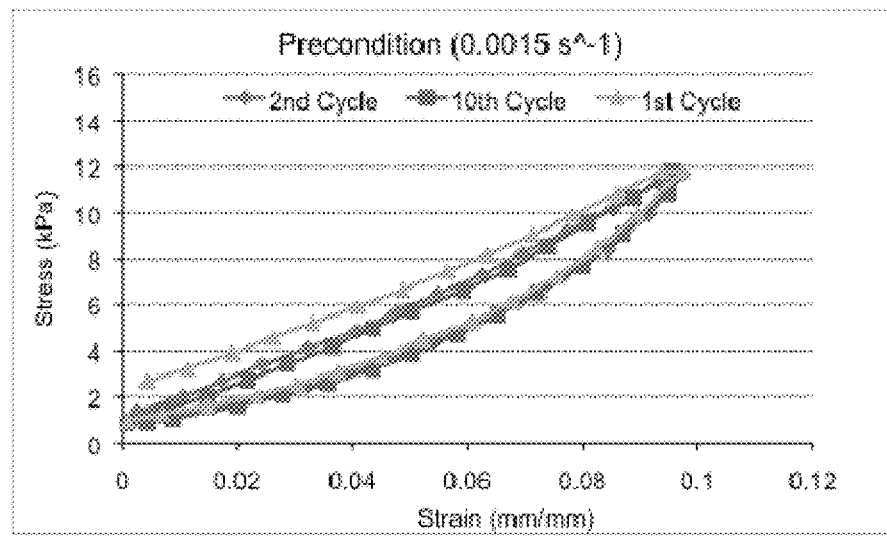

Unconfined compression analysis was performed by inputting a ramp strain until a given value (10% strain) was reached. Then compression was held until stress reaches equilibrium. FIGS. 16A and 16B are graphs showing the compressive behavior for a native canine TMJ disc and for a pre-implantation UBM construct, respectively. Of note, the UBM construct behaves more elastically than the native disc. The native TMJ disc was observed to absorb water during unloading.

Figure 17A:
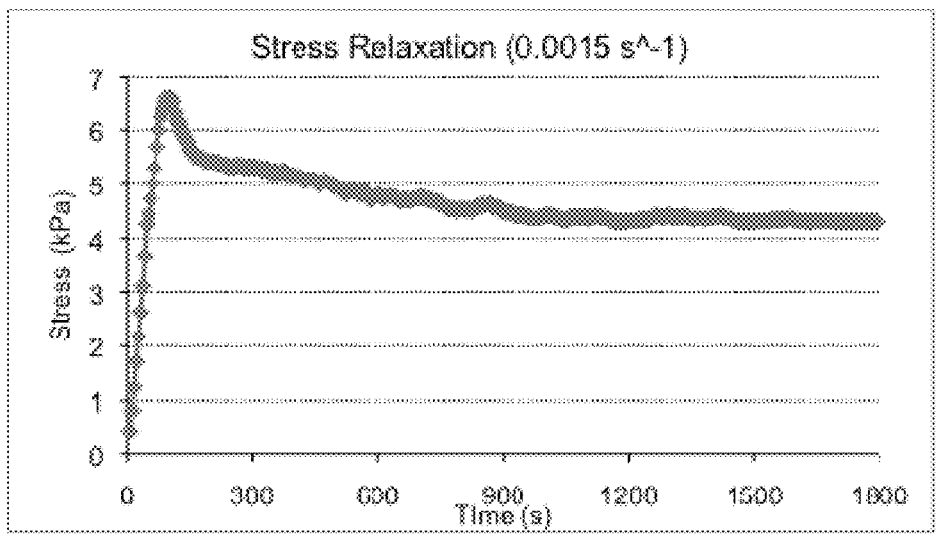
FIGS. 17A and 17B are graphs showing the relaxation data for native canine TMJ and preimplanted UBM, respectively.
Figure 17B:
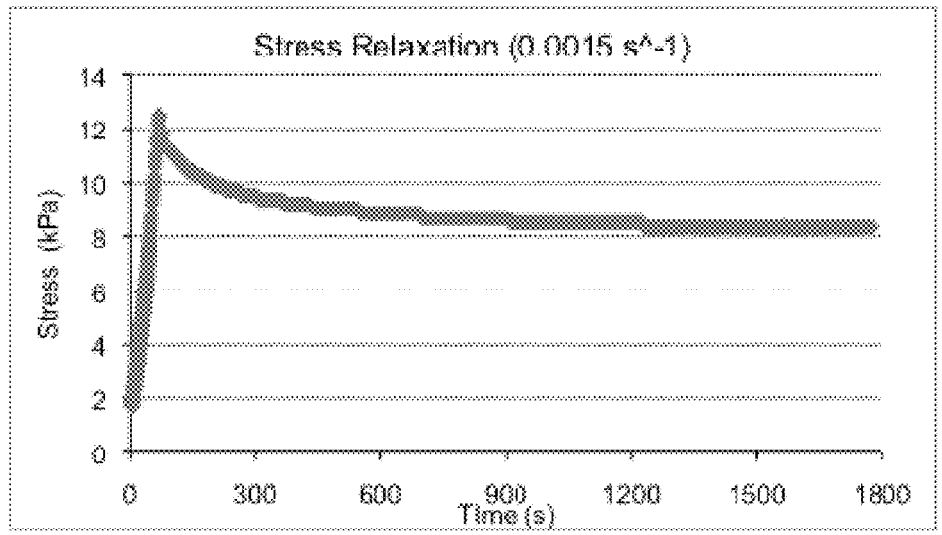
Figure 18:
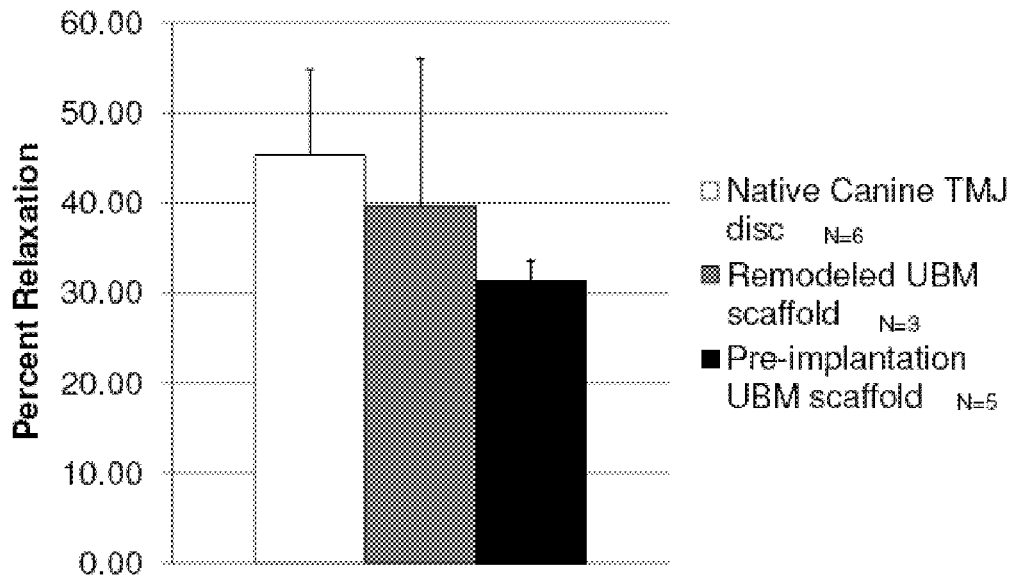
FIG. 18 is a graph showing percent relaxation for native canine TMJ, pre-implantation UBM and remodeled UBM scaffold at 6 months post-implantation.

Percent relaxation over time was determined for native TMJ and preimplantation UBM. In this method, a pre-load of 0.1N for 30 mins is applied and the specimen height was determined. Then, preconditioning between 0-10% strain at 9%/min strain rate (slow) was performed. This yielded repeatable data. Then, stress-relaxation of 10% strain was performed and the sample was allowed to relax for 30 mins. FIGS. 17A and 17B are graphs showing the relaxation data for native canine TMJ and preimplanted UBM, respectively. Both showed very similar viscous behavior, though the UBM implant had a higher elastic response. FIG. 18 shows percent relaxation for native canine TMJ, pre-implantation UBM and remodeled UBM scaffold at 6 months. No significant differences in percent relaxation were seen.

Figure 19:
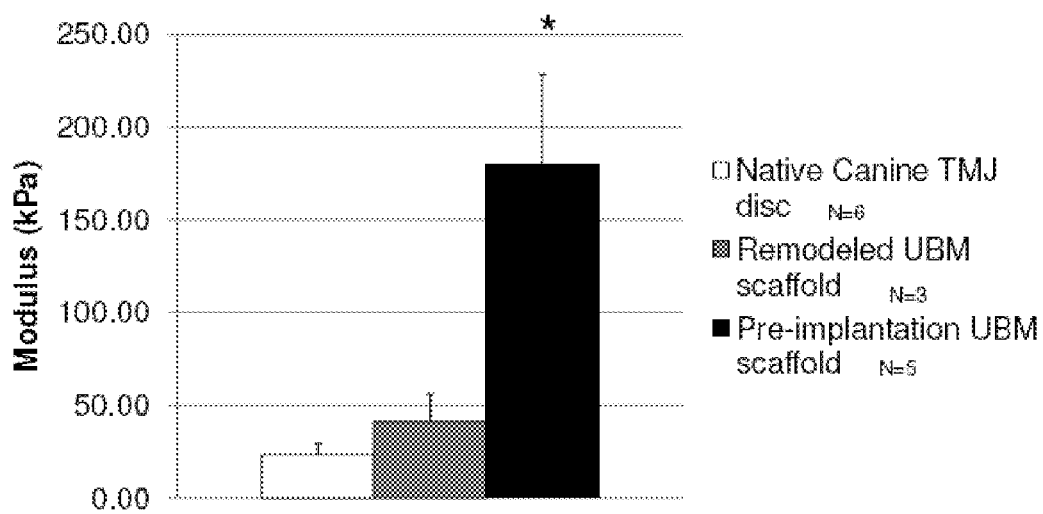
FIG. 19 is a graph showing the Tangent Modulus for native canine TMJ, pre-implantation UBM and remodeled UBM scaffold at 6 months post-implantation.

The Tangent Modulus is slope of linear region of stress-strain curve. Tangent Modulus was determined for native canine TMJ, pre-implantation UBM and remodeled UBM scaffold at 6 months. FIG. 19 is a graph showing the Tangent Modulus. Notably, the remodeled UBM implant was twice as stiff as the native TMJ at 6 months post implantation; however these results were not statistically significant. These results suggest that the initially stiffer UBM implant is remodeling with mechanical properties that resembled those observed for the native meniscus at 6 months post-implantation. The pre-implantation scaffold is much stiffer than native canine TMJ or remodeled UBM.

Biochemistry

Figure 20:
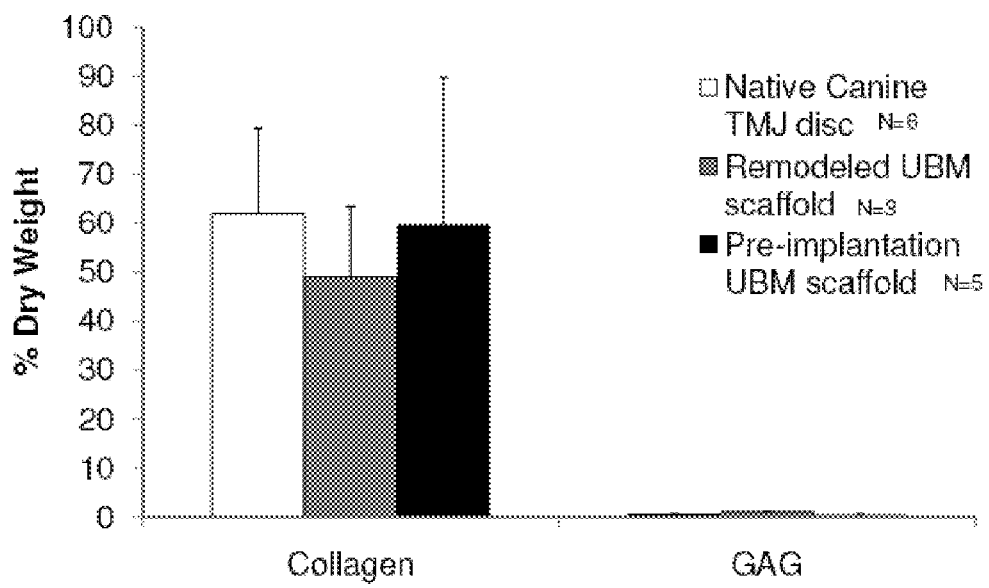
FIG. 20 is a graph showing Collagen and GAG content for native canine TMJ, pre-implantation UBM and remodeled UBM scaffold at 6 months post-implantation.
Figure 21:
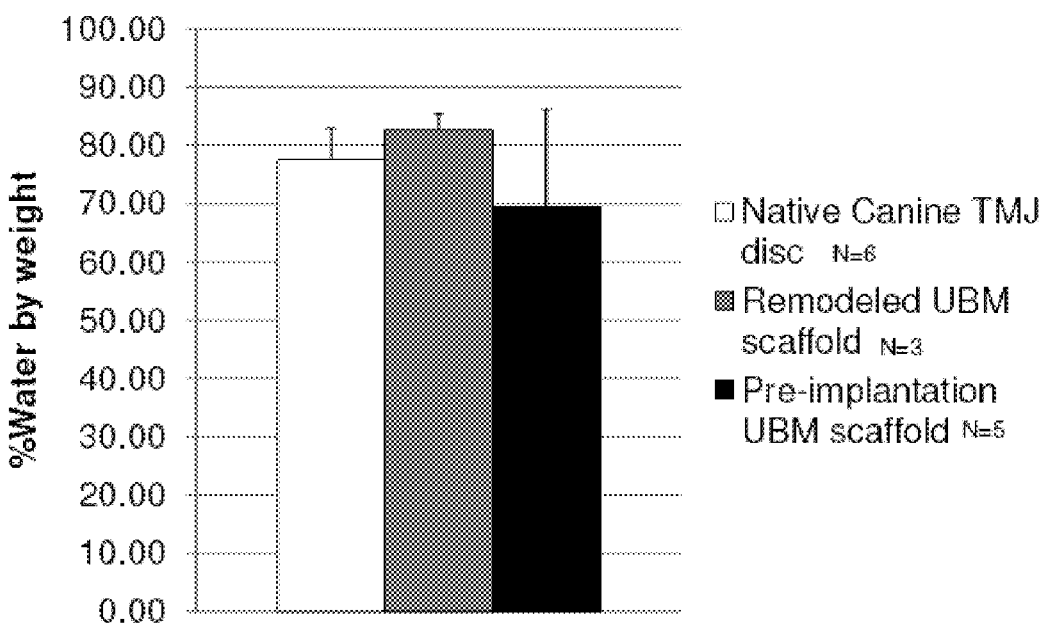
FIG. 21 is a graph showing water content for native canine TMJ, pre-implantation UBM and remodeled UBM scaffold at 6 months post-implantation.

The tested samples were analyzed for collagen, GAG and water content. Collagen content was assessed using a hydroxyproline assay, GAG content was assessed using a dimethylene blue assay, and water content was assessed by measuring sample weight both pre- and post-lyophilization of the tissue to remove water content. FIG. 20 is a graph showing Collagen and GAG content for native canine TMJ, pre-implantation UBM and remodeled UBM scaffold at 6 months. FIG. 21 is a graph showing water content for native canine TMJ, pre-implantation UBM and remodeled UBM scaffold at 6 months. There was no significant difference in collagen, GAG and water content for all samples.

FIG. 22A is a tablulation of the data from Example 2. FIG. 22B provides averages and standard deviation.

Example 5

Replacing a Human TMJ Meniscus with an ECM Scaffold

Patients whose TMJ meniscus is determined to be irreparably damaged, or that failed previous meniscus replacement with other autogenous or alloplastic materials are considered for this procedure. The patient is placed under a general anesthetic. The irreparably damaged human TMJ meniscus is surgically excised through a standard preauricular incision. Next, any adhesions on the undersurface of the glenoid fossa are removed with a curette, and bony spurs on the articulating surface of the condyle are conservatively removed with a rongeur. The articulating eminence is smoothed of any irregularities via a bone file. Next, the appropriate size scaffold is surgically implanted with slow-resorbing sutures to both the root of the zygomatic arch and the adjacent muscle tissue. The mandible is manipulated through a sterile drape to ensure the appropriate fit and coordinated movement of the implant relative to the condyle and fossa. The surgical field is irrigated with an antibiotic solution prior to being sutured in layers. The wound is closed in layers and the patient is placed on an appropriate antibiotic (e.g., KEFLEX™, if not penicillin allergic) and analgesic (e.g., NSAID, and narcotic of the physician's choice for breakthrough pain) for seven days. Physical therapy for the mandible is initiated by at least the fourth postoperative day.

Having described this invention, it will be understood to those of ordinary skill in the art that the same can be performed within a wide and equivalent range of conditions, formulations and other parameters without affecting the scope of the invention or any embodiment thereof.

We claim:

1. A bioscaffold for replacement or regeneration of a temporomandibular joint meniscus, the bioscaffold comprising:
   a biocompatible, biodegradable, elastomeric implant dimensioned to fit within the TMJ and mimic the size and function of a native TMJ meniscus, the implant comprising a top sheet formed from one or more layers of a biocompatible material, a bottom sheet formed from one or more layers of the biocompatible material, and a raised central core consisting essentially of an acellular and noncrosslinked extracellular matrix disposed between the top and bottom sheets, wherein the top sheet and bottom sheet have substantially the same thickness, and further wherein the top and bottom sheets radially extend from the raised central core to form a brim having surgical attachment sites in the brim;
   wherein the central core has a circular base with a diameter, or an elliptical base with a major diameter and a minor diameter, and a height and composition of the central core that permits the core to deform under stress, and the diameter or the major and minor diameter is sufficient for the core to carry shear forces between the mandible and the skull when the implant is affixed to an articulating surface in the TMJ.

2. The bioscaffold of claim 1, wherein at least one of the top or bottom sheets is formed from two layers of biocompatible material encapsulating the core.

3. The bioscaffold of claim 1, wherein the core is encased in a plurality of layers of extracellular matrix.

4. The bioscaffold of claim 1, wherein the core comprises a gel or particulate extracellular matrix that is encased in a plurality of layers of extracellular matrix, wherein the gel or particulate extracellular matrix within the core allows compression of the core.

5. The bioscaffold of claim 4, wherein the core comprises the particulate extracellular matrix encased in the plurality of layers of extracellular matrix.

6. The bioscaffold of claim 5, wherein the particulate extracellular matrix of the core comprises particles having a particle size from 10 to 400 microns.

7. The bioscaffold of claim 6, wherein the particles have an average particle size of 150 to 200 microns.

8. The bioscaffold of claim 1, wherein the bioscaffold additionally comprises a synthetic polymer that imparts flexibility to the bioscaffold.

9. The bioscaffold of claim 1, wherein the core is concave, convex, biconcave, biconvex, or a combination thereof.

10. The bioscaffold of claim 1, wherein both the core and the top and bottom sheets comprise acellular and non-crosslinked extracellular matrix of tissue selected from the group consisting of small intestine, urinary bladder, esophagus, skin, liver, spleen, heart, pancreas, ovary, and arteries.

11. The bioscaffold of claim 1, wherein the central core has an elliptical base with a major diameter and a minor diameter.

12. A bioscaffold for replacement or regeneration of a temporomandibular joint meniscus, the bioscaffold comprising:
a biocompatible, biodegradable, elastomeric implant dimensioned to fit within the TMJ and mimic the size and function of a native TMJ meniscus, the implant comprising a top sheet formed from one or more layers of biocompatible material, a bottom sheet formed from one or more layers of biocompatible material, and a central core disposed between the top and bottom, wherein the core comprises acellular and non-crosslinked extracellular matrix particles or gel and the core extends between the top or bottom sheets to form a nonplanar pillow having a height of between 0.5 and 4 cm, wherein the core has a circular base with a diameter, or an elliptical base with a major diameter and a minor diameter, and the height and composition of the core permits the core to deform under stress, and the diameter or major and minor diameter of the core is sufficient for the core to carry shear forces between the mandible and the skull when the implant is affixed to an articulating surface in the TMJ; and
wherein the top sheet and bottom sheet extend outwardly from the core to form a brim with surgical attachment sites in the brim.

13. The bioscaffold of claim 12, wherein the core comprises a plurality of layers of extracellular matrix.

14. The bioscaffold of claim 13, wherein the core pillow is shaped concave, convex, biconcave, biconvex, or a combination thereof.

15. The bioscaffold of claim 14, wherein the core comprises a convex pillow extending from the base.

16. The bioscaffold of claim 15, wherein the core comprises a deformable gel.

17. The bioscaffold of claim 16, wherein the extracellular matrix is an extracellular matrix gel that gels at a temperature at or above 25 degrees Celsius.

18. The bioscaffold of claim 12, wherein core comprises deformable particulate extracellular matrix particles having a particle size from 10 to 400 microns.

19. The bioscaffold of claim 18, wherein the particles have an average particle size of 150 to 200 microns.

20. The bioscaffold of claim 12, additionally comprising a synthetic elastomeric polymer.

21. The bioscaffold of claim 12, wherein both the core and the top or bottom sheets comprise extracellular matrix of tissue selected from the group consisting of small intestine, urinary bladder, esophagus, skin, liver, spleen, heart, pancreas, ovary, and arteries.

22. The bioscaffold of claim 12, wherein at least a portion of the top or bottom sheets comprises basement membrane.

23. The bioscaffold of claim 12, wherein the at least one of the top or bottom sheets has an inner surface and an outer surface, and wherein at least a portion of the outer surface comprises basement membrane.

24. A bioscaffold for replacement or regeneration of a temporomandibular joint (TMJ) meniscus the bioscaffold comprising:
a biocompatible, biodegradable, elastomeric implant dimensioned to fit within the TMJ and mimic the size and function of a native TMJ meniscus, the implant comprising a top sheet formed from one or more layers of biocompatible material, a bottom sheet formed from one or more layers, and a raised central elastomeric core comprising acellular and noncrosslinked extracellular matrix particles or gel disposed between the top and bottom sheets, wherein the core is deformable under stress to cushion forces between the mandibular condyle and the skull bones with which it articulates when the implant is affixed to an articulating surface in the TMJ
and wherein the top and bottom sheets radially extend from the core to form a brim comprising one or more surgical attachment sites; wherein the core is 8-12 mm wide, and the implant is 16-20 mm wide; and wherein the core comprises a circular base with a diameter or an elliptical base with a major diameter and a minor diameter, whereby the core can carry shear forces between the mandible and skull when the implant is affixed to the articulating surface.

25. The bioscaffold of claim 24, wherein the core comprises particulate extracellular matrix and is encased in a plurality of layers of extracellular matrix.

26. The bioscaffold of claim 24, wherein the core extends from the base in a shape that is concave, convex, biconcave, biconvex, or any combination thereof.

27. The bioscaffold of claim 24, wherein core comprises particulate extracellular matrix having a particle size from 10 to 400 microns.

28. The bioscaffold of claim 27, wherein the particulate extracellular matrix has an average particle size of 150 to 200 microns.

29. The bioscaffold of claim 27, additionally comprising a synthetic elastomeric polymer.

30. The bioscaffold of claim 24, wherein the extracellular matrix is an extracellular matrix gel that gels at a temperature at or above 25 degrees Celsius.

31. A bioscaffold for replacement or regeneration of a temporomandibular joint meniscus, the bioscaffold comprising:
a biocompatible, biodegradable, elastomeric implant dimensioned to fit within the TMJ and mimic the size and function of a native TMJ meniscus, the implant comprising a top sheet formed from one or more layers of a biocompatible material, a bottom sheet formed from one or more layers of the biocompatible material, and a central core comprising an acellular and noncrosslinked extracellular matrix gel, or particles having a particle size from 10 to 400 microns, disposed between the top and bottom sheets, wherein the top sheet and bottom sheet have substantially the same thickness, and further wherein the top and bottom sheets extend around the central core to form a brim having surgical attachment sites in the brim;
wherein the central core has an elliptical base with a major diameter and a minor diameter, and the central core extends away from the brim in a shape that is concave, convex, biconcave, biconvex, or any combination thereof and a height and composition of the central core permits the core to deform under stress, and central core with the elliptical base is elongated along the major diameter for the core to carry shear forces between the mandible and the skull when the implant is affixed to an articulating surface in the TMJ.

32. The bioscaffold of claim 31 wherein the central core comprises the particles, wherein the particles have an average particle size of 150 to 200 microns.

33. The bioscaffold of claim 32, wherein the central core extends 0.4 to 4 cm from the brim, has a major diameter of 8-12 mm, and the implant is 16-20 mm wide.

* * * * *